(12) United States Patent
Pilcher et al.

(10) Patent No.: US 7,320,691 B2
(45) Date of Patent: Jan. 22, 2008

(54) APPARATUS AND METHOD FOR ACOUSTIC/MECHANICAL TREATMENT OF EARLY STAGE ACNE

(75) Inventors: Kenneth A. Pilcher, Seattle, WA (US); David Giuliani, Mercer Island, WA (US); Stephen M. Meginniss, Seattle, WA (US)

(73) Assignee: Pacific Bioscience Laboratories, Inc., Bellevue, WA (US)

( * ) Notice: Subject to any disclaimer, the term of this patent is extended or adjusted under 35 U.S.C. 154(b) by 536 days.

(21) Appl. No.: 10/345,909

(22) Filed: Jan. 15, 2003

(65) Prior Publication Data

US 2005/0277950 A1 Dec. 15, 2005

(51) Int. Cl.
*A61B 17/50* (2006.01)
(52) U.S. Cl. .................. 606/131; 604/289; 604/313
(58) Field of Classification Search ............... 606/131; 604/289, 290, 313; 15/28; 310/36
See application file for complete search history.

(56) References Cited

U.S. PATENT DOCUMENTS

| | | | |
|---|---|---|---|
| 3,750,279 A * | 8/1973 | Cobarg et al. ............... 30/43.9 |
| 3,756,105 A * | 9/1973 | Balamuth et al. ............... 83/14 |
| 4,158,246 A | 6/1979 | Meadows et al. |
| 4,203,431 A | 5/1980 | Abura et al. |
| 4,670,931 A | 6/1987 | Abbassi |
| 5,186,627 A | 2/1993 | Amit et al. |
| 5,467,495 A | 11/1995 | Boland et al. |
| 5,624,416 A * | 4/1997 | Schatz ........................ 604/313 |
| 5,687,442 A | 11/1997 | McLain |
| 5,697,115 A | 12/1997 | Sciarra et al. |
| 5,891,063 A * | 4/1999 | Vigil ........................ 601/114 |
| 5,931,814 A * | 8/1999 | Alex et al. .................. 604/131 |
| 6,021,538 A | 2/2000 | Kressner et al. |
| 6,032,313 A | 3/2000 | Tsang |
| 6,253,405 B1 | 7/2001 | Gutelius et al. |
| 6,343,396 B1 * | 2/2002 | Simovitz et al. ............... 15/27 |
| 6,363,565 B1 | 4/2002 | Paffrath |
| 6,564,940 B2 | 5/2003 | Blaustein et al. |
| 6,569,170 B1 | 5/2003 | Kellogg |
| 6,575,924 B2 | 6/2003 | Wevers et al. |
| 6,645,184 B1 | 11/2003 | Zelickson et al. |
| 6,836,917 B2 | 1/2005 | Blaustein et al. |
| 2002/0040199 A1 | 4/2002 | Klopotek |
| 2002/0049399 A1 | 4/2002 | Stampf |
| 2002/0107527 A1 | 8/2002 | Burres |
| 2003/0125754 A1 | 7/2003 | Davis et al. |
| 2005/0199265 A1 | 9/2005 | France et al. |

FOREIGN PATENT DOCUMENTS

WO WO2003096860 11/2003

* cited by examiner

*Primary Examiner*—Michael J. Hayes
*Assistant Examiner*—Nguyen Victor
(74) *Attorney, Agent, or Firm*—Jensen & Puntigam, P.S.

(57) ABSTRACT

The apparatus includes at least two skin-contacting elements, the elements having narrow end faces and a mounting assembly for holding the elements closely adjacent to each other. A driving assembly reciprocally moves one element relative to the adjacent element(s) at a frequency that produces an action on the pores of the skin to loosen sebaceous plugs present in the pores, by permitting their ready removal from the skin.

52 Claims, 19 Drawing Sheets

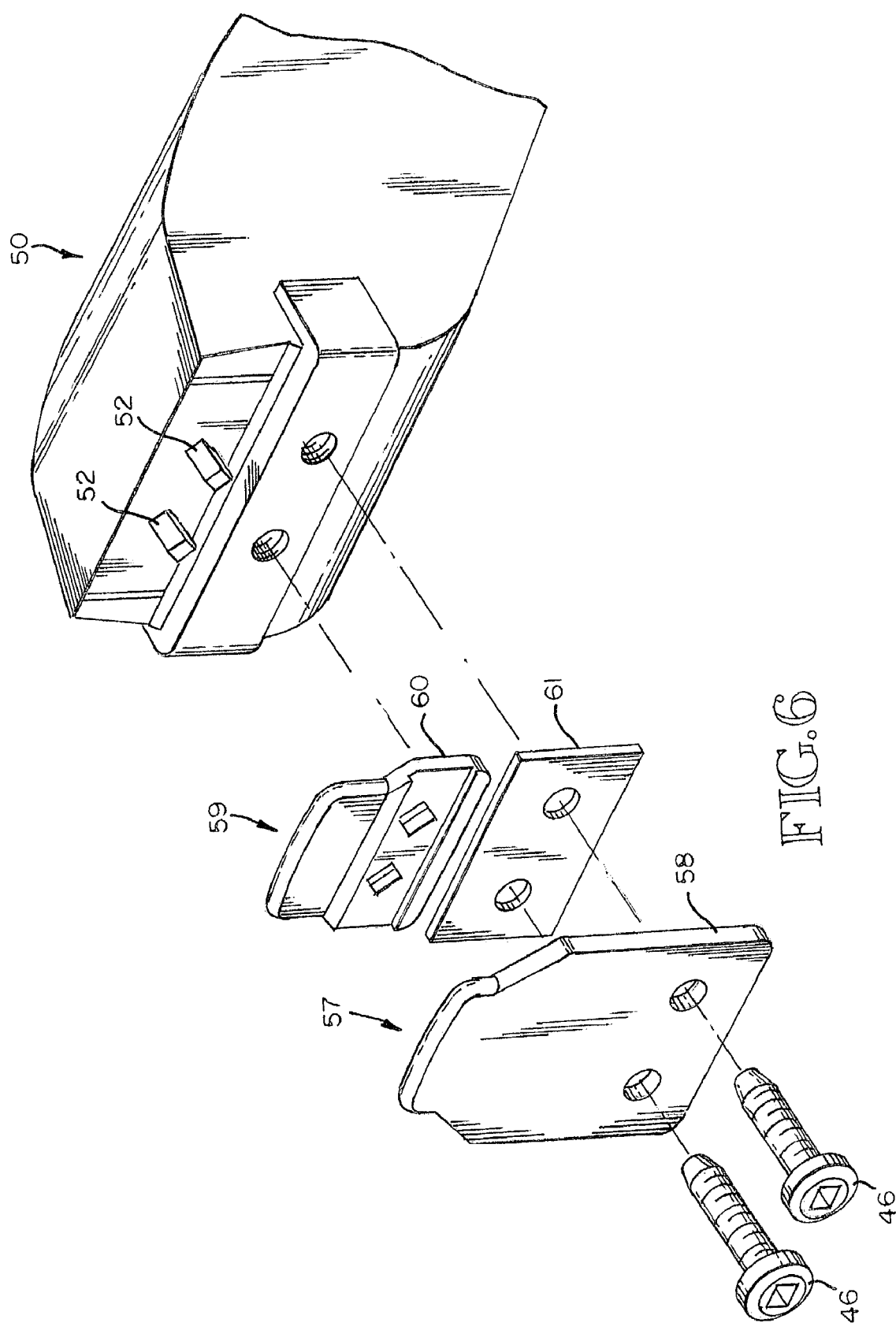

FIG.13A
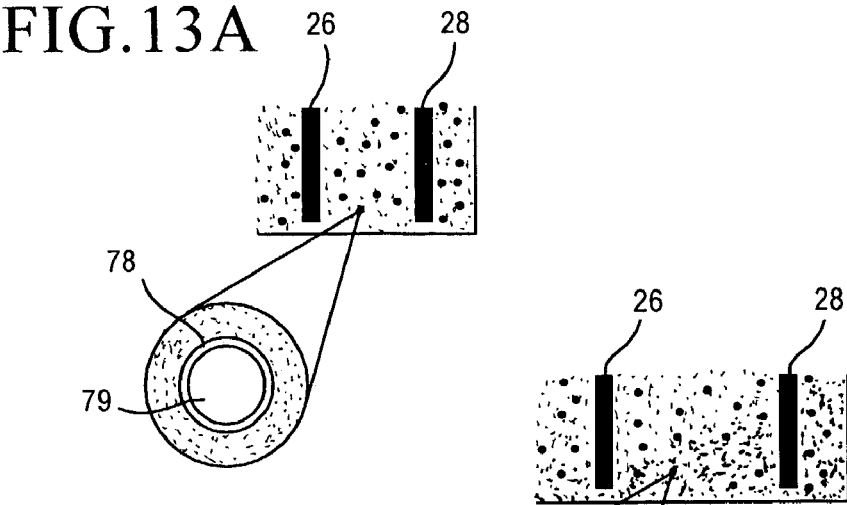
FIG.13B
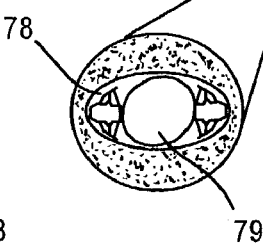
FIG.13C
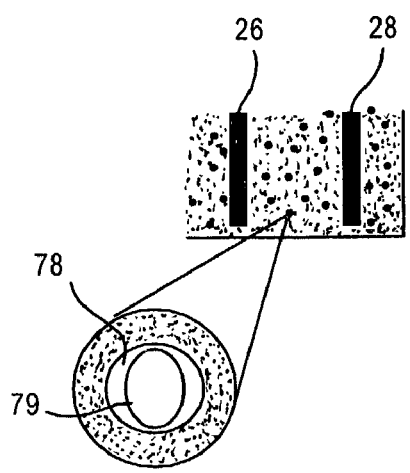
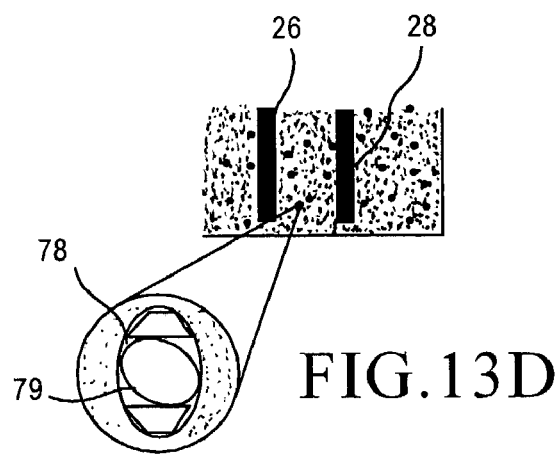
FIG.13D

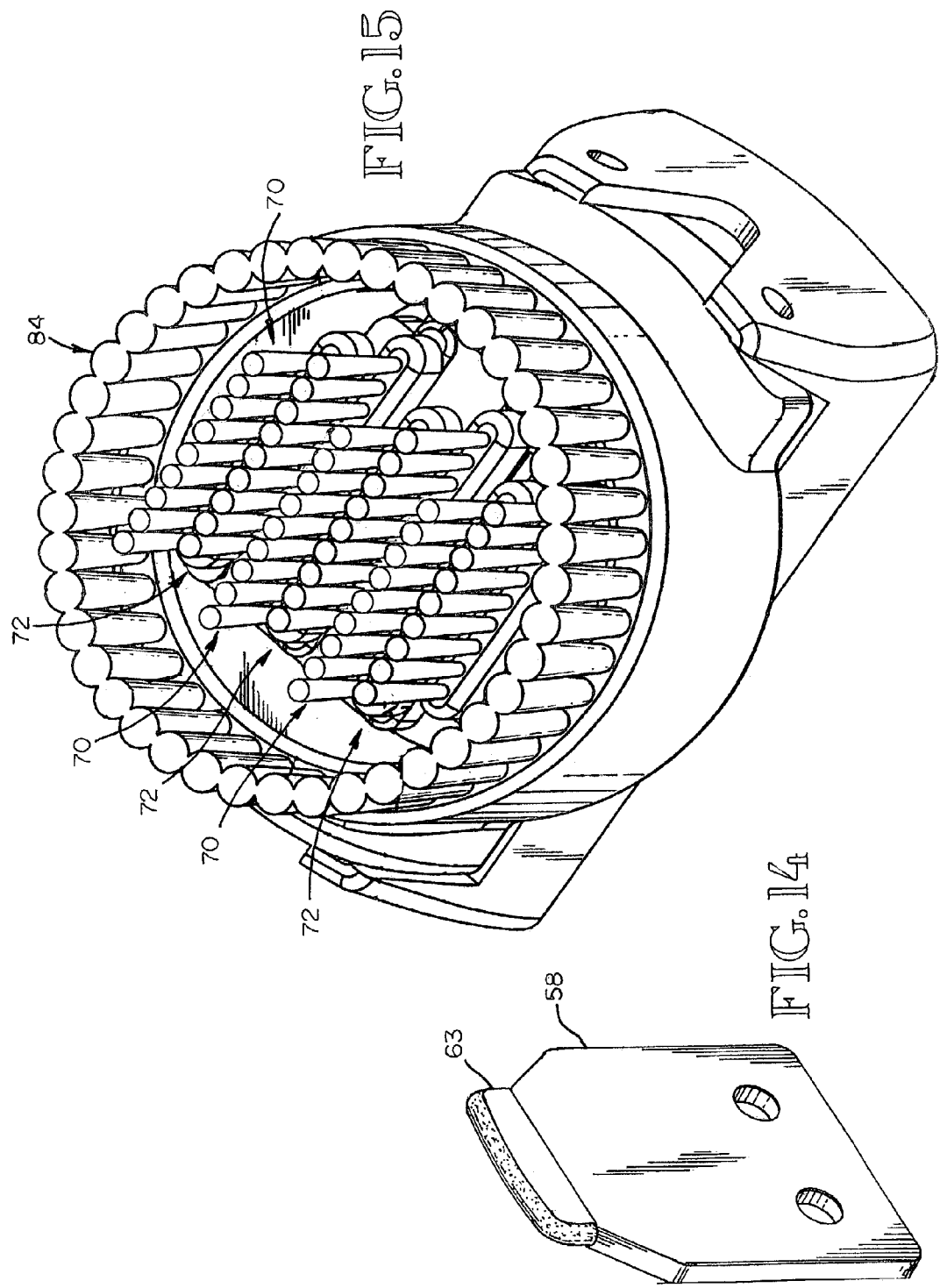

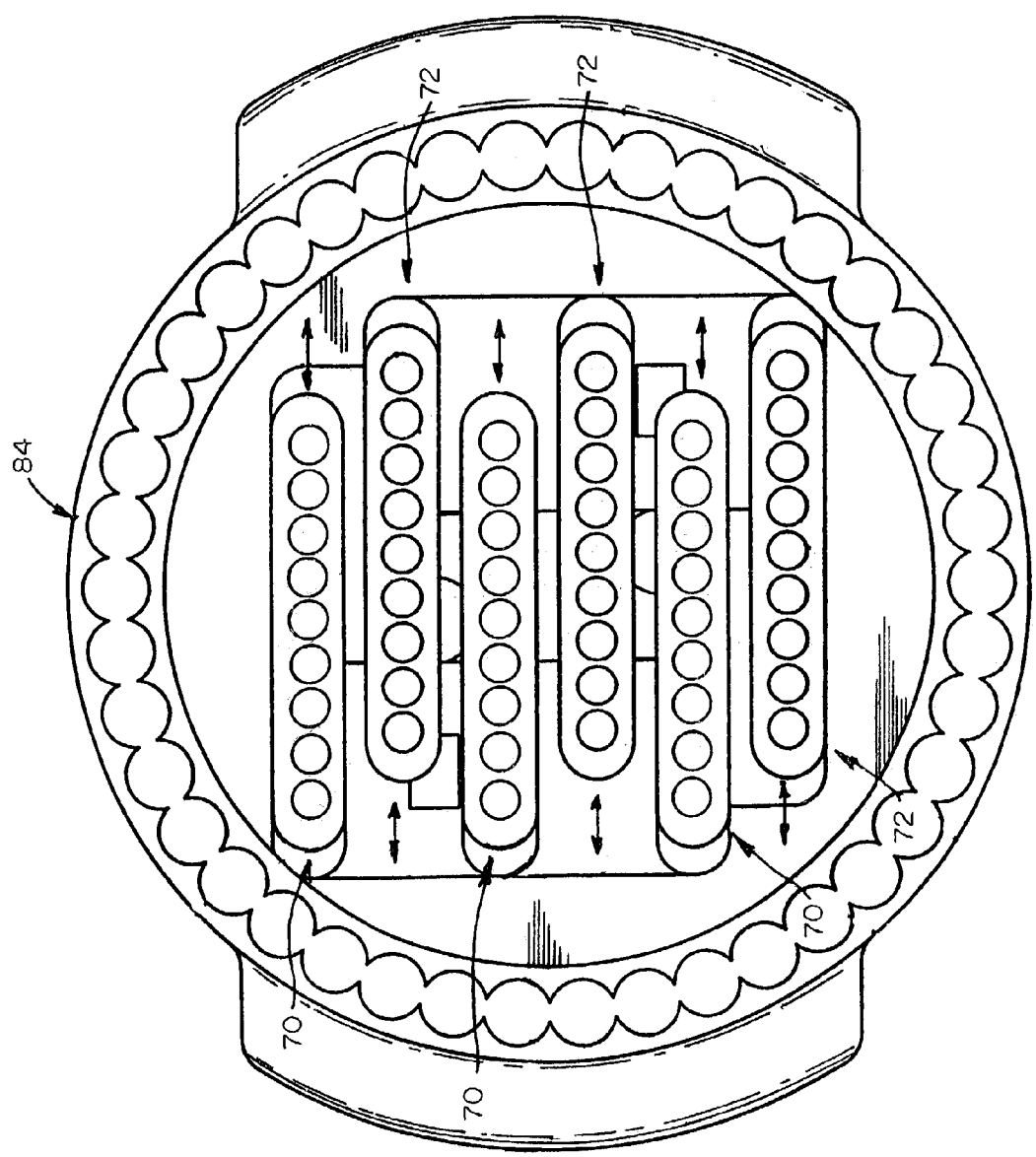

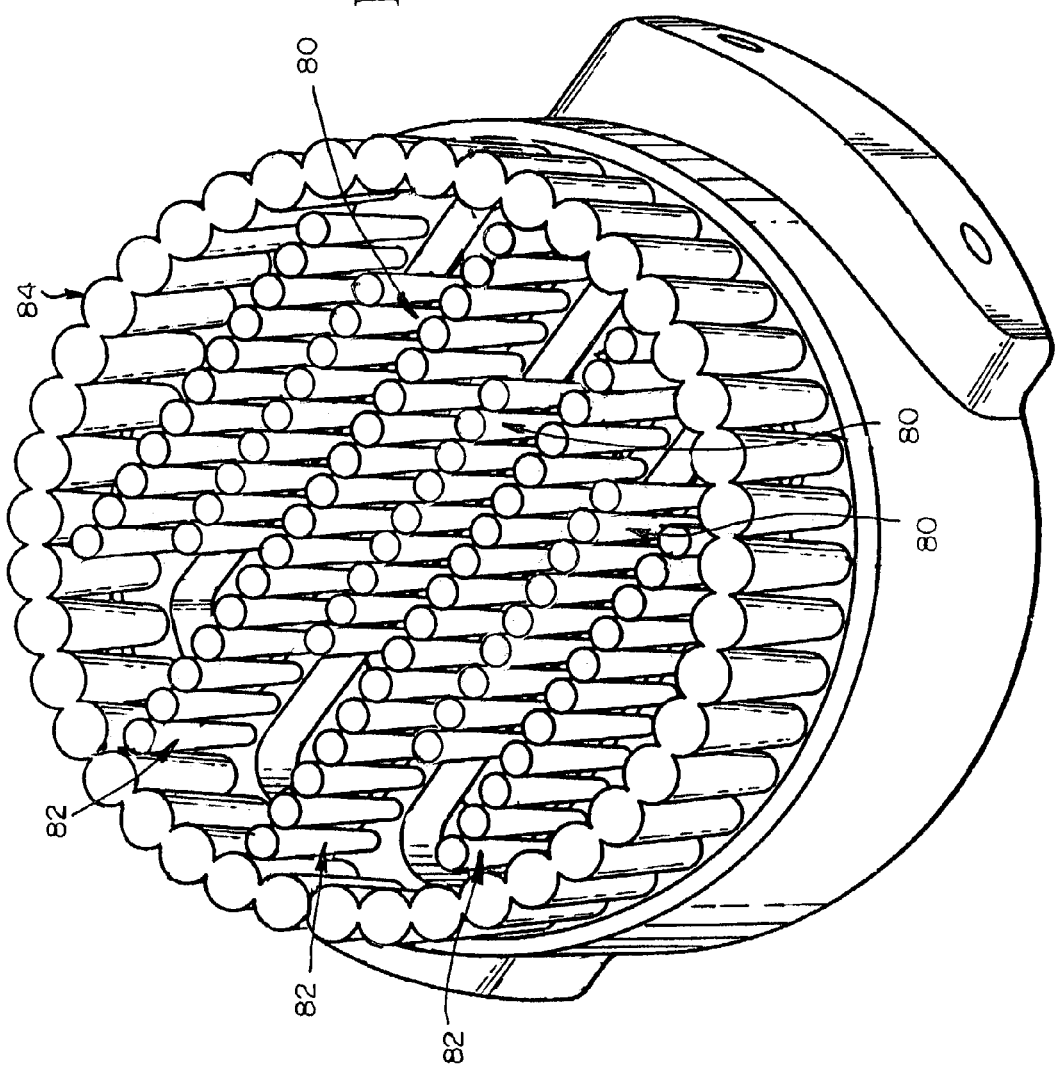

APPARATUS AND METHOD FOR ACOUSTIC/MECHANICAL TREATMENT OF EARLY STAGE ACNE

TECHNICAL FIELD

This invention relates generally to treatment of early stage acne, and more particularly concerns mechanical and/or acoustic devices for applying energy to the skin in the vicinity of the early stage acne lesion, i.e. the sebaceous plug.

BACKGROUND OF THE INVENTION

Common acne, known more specifically as acne vulgaris, is generally regarded to be the most treated skin condition in the United States. Prompt and appropriate treatment of acne, particularly in its early stages, is important for both resolving the early stage condition and preventing more severe acne conditions, which have possible permanent effects, including the possibility of severe scarring. While acne can occur in men and women of all ages, it typically occurs in adolescents and young adults.

The earliest evidence of acne is the formation of a sebaceous plug. The sebaceous plug, which is formed in the individual skin pores (follicles), is typically not visible to the unassisted eye, but can be seen under a microscope or other optical lens device. It is formed when a combination of corneocytes and sebum, which are both natural components of the skin, block the pore opening, and specific colonies of bacteria within the skin pore then expand in numbers. The plug of cells and sebum may adhere to the wall of the skin pore, leading to material aggregation in the pore, and subsequent widening of the pore. This situation may in turn result in the further accumulation of sebum and other cellular material, and the eventual possible rupture of the follicular wall, followed by an inflammatory response and the subsequent formation of inflamed papules and inflamed pustules, typically referred to as pimples.

Existing systemic treatments of acne include oral antibiotics, retinoids and hormonal treatments. Each of these treatments, while effective to various extents, has its own significant side effects and disadvantages. For instance, oral antibiotic treatment reduces the number of bacteria in the skin pores, but does not decrease the rate of sebum secretions or the actual number of the sebaceous plugs formed. Disadvantages of the various treatments include various undesirable skin reactions, including skin dryness, fluid loss and possible hair loss. Typically, all such treatments irritate the skin to some extent.

PRIOR ART

Prior art concerning localized treatment for acne can be classified generally as "mechanical" or "chemical."

Mechanical methods include vacuum devices, mechanized scrub brushes and manual loop-like instruments, such as shown in U.S. Pat. Nos. 5,624,416 and 4,175,551. Use of these devices is typically site-specific and usually requires a specific technique, making them difficult to use. Methods that use heat generated by electrical resistance or ultrasound are also known, such as shown in U.S. Pat. No. 6,245,093. Still other methods claim to be able to kill target micoorganisms, including those that cause acne, using selected frequencies of electrical current, such as shown in U.S. Pat. No. 5,891,182.

In the beauty/skin care industry, the use of micro-abrasion is also a popular treatment for "rejuvenating" skin. However, this technique of removing some layers of the cornified skin layer by abrasive materials can cause intense irritation.

Chemical methods for acne, including topical and systemic treatments and their possible side effects, are listed in Tables I and II below, respectively.

TABLE I

Common Topical Acne Treatments

| Treatment | Possible Side Effect |
|---|---|
| Soaps and detergents to remove sebum from skin surface | Drying of skin surface (xerosis) if used in excess |
| Astringents and short chain alcohols to remove oily materials and water in upper epidermal areas | Drying of the skin surface and breakdown of the skin's barrier function, and eventual microbial entrance into the body |
| Antibacterial agents (e.g. benzoyl peroxide, salicylic acid), that can destroy bacteria when the agent is in immediate contact with the microorganisms | <5% penetrates into the pores, with the rest possibly interacting with corneocytes causing irritation and erythema (red skin), and contact dermatitis |

TABLE II

Common Systemic Acne Treatments

| Treatment | Possible Side Effect |
|---|---|
| Oral antibiotics | Photosensitivity, gastrointestinal problems, and bacterial antibiotic resistance |
| Hormonal manipulations to control sebaceous gland size and secretion rate by regulating androgens and estrogens | Increased risk of thromboembolism, feminization in men, and other undesirable effects. |
| Retinoids, which likely change the cohesiveness of follicular epithelial cells | Teratogenic, and other strong negative side effects |

With the present apparatus, conditions that lead to early stage acne are prevented and early stage acne is effectively treated by maintaining or restoring the pore openings to an open state, to allow continuing exudation from the sebaceous gland, to encourage maintaining an aerobic state within the pore, and to prevent the development of more severe acne conditions, without the inconvenience, side effects and other limitations present in existing treatments.

DISCLOSURE OF THE INVENTION

Accordingly, the invention is an apparatus for the treatment of acne, comprising: at least two contacting elements having end faces which are in substantially the same plane, wherein at least one contacting element is a moving contacting element; a mounting assembly for holding the contacting elements substantially adjacent to each other; and an assembly for reciprocally moving said at least one moving contacting element relative to at least one adjacent contacting element, wherein when the apparatus is positioned so that the end faces of the contacting elements contact the skin, an action on the skin is produced to remove sebum plugs from skin pores, permitting ready removal thereof from the skin.

The contacting elements can comprise either elements of rigid material, compliant material or rows of bristle tufts. The apparatus further can be used for an effective cleansing treatment of skin which does not have an acne condition. Still further, the apparatus could comprise a single moving contact element.

Another aspect of the invention is a method for treatment of skin comprising the steps of: a first step of deforming the skin from a neutral position to a first deformed position at which point the skin has reached approximately its elastic limit; a second step permitting the skin to return to said neutral position; and repeating the first, second steps, within a frequency range of 20 Hz to 1 kHz, to produce an action on the skin which results in the cleansing of the skin, including removal of undesired material from skin pores. The method is effective for acne treatment as well as general skin cleansing.

BRIEF DESCRIPTION OF THE DRAWINGS

FIG. 6 is an exploded view of one embodiment of the mechanical acne treatment device of the present invention.

FIGS. 13A, 13B, 13C and 13D show the effect on a sebaceous plug positioned in a skin pore subjected to the action of the apparatus of FIGS. 10-12.

FIG. 14 shows a variation of the mechanical device shown in FIG. 7, wherein a compliant material is applied to the contact element surface.

FIG. 15 is a diagram showing an alternate embodiment of the present invention with alternately linearly movable rows of bristle tufts, surrounded by a circular row of fixed bristle tufts.

FIG. 16 is a top view of the device shown in FIG. 15.

FIG. 17 is a diagram shown a variation of the mechanical device shown in FIG. 15, in which one set of bristle tufts is fixed, and the other set moves linearly.

BEST MODE FOR CARRYING OUT THE INVENTION

Figure 1:
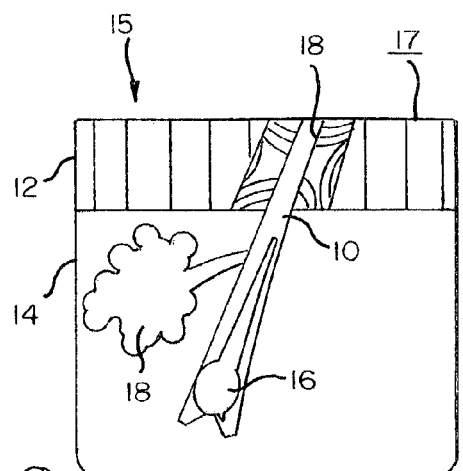
FIG. 1 shows a cross-sectional view of a typical skin pore.
Figure 2:
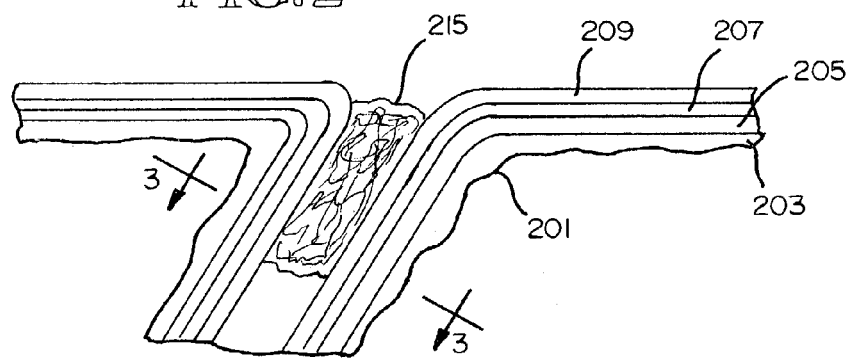
FIG. 2 is a cross-sectional view of a comedone-plugged acroninfundibulum.

FIG. 1 is a representation of a typical skin pore, including the epidermis and dermis layers of the skin. The skin pore 10, also referred to as a follicle, includes a normal hair 16 and an associated sebaceous gland 18. The sebaceous gland 18 normally produces sebum lipids. The production of sebum, however, is typically not sufficient alone to result in acne. Further, acne lesions do not occur if the sebum lipids are free to reach the surface of the skin. However, when the skin pore or follicle becomes blocked, such as by an overproduction of corneocytes, or inadequate shedding of the corneocytes (as shown in FIG. 2), the balance of the skin system is upset. The blocked follicles lead to the formation of closed, but non-inflamed, sebaceous plugs. The sebaceous plug (microcomedone) 215 shown in vertical cross-sectiona in FIG. 2 and in horizontal cross-section in FIG. 3 forms in the acroinfundibulum portion of the follicle, which is the upper portion of the follicle.

Following the initial formation of the sebaceous plug, if the pH and oxygen tension are within certain ranges below the closed sebaceous plug, the number of Propionibacteria acnes bacteria expands, leading to a pathogenic condition. This leads further to a sequence of actions and reactions within the follicle, including damage to the follicular wall, comprising skin layers 201, 203, 205, 207 and 209, and extrusion of accumulated materials into the dermis portion of the skin, resulting in an inflammatory response which leads to skin lesions and pustules.

In the present invention, the focus is on maintaining the acroinfundibulum portion of the follicle in an open state, which eliminates the environment in which the acne bacteria can thrive within the follicle, and encourages establishing an aerobic state within the follicle, while at the same time minimizing the amount of sebum that can accumulate within the infundibulum portion of the follicle.

Figure 3:
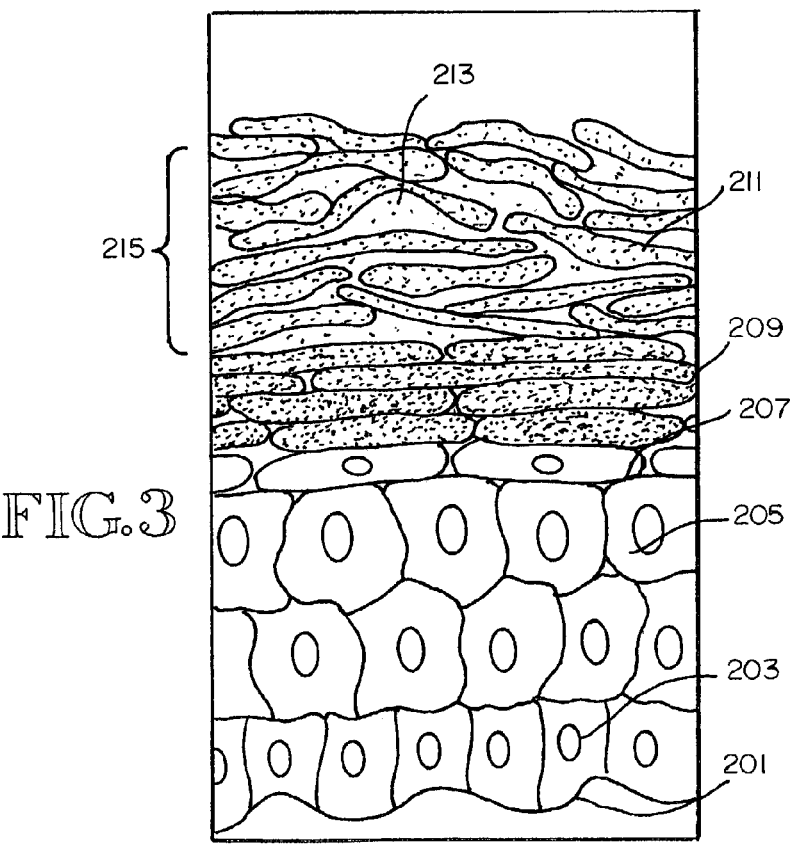
FIG. 3 is a cross-sectional view of the comedone-plugged acroinfundibulum, taken along lines 3-3 in FIG. 2.

The basic approach of the present invention is to reopen the individual pores that may have been blocked by the plug of corneocytes 211 and sebum lipids 213 (FIG. 3). It is based on the discovery that application of differential motion locally to the pore opening will open a blocked pore. The opening of the pore is due to the fact that the blocking materials within the follicles have different physical properties than the wall of the infundibulum and the surrounding skin. With the present invention, the skin area is deformed slightly and then released to a relaxed position and then deformed slightly in the opposite direction and then again released to a relaxed position, at a specific frequency, which results in the plugs being loosened from their position in the skin pores. The loosened plugs can then be readily removed, such as by wiping or washing, permitting thereafter normal skin secretion of lipids, and consequently avoiding the consequences of more fully developed acne.

Figure 4:
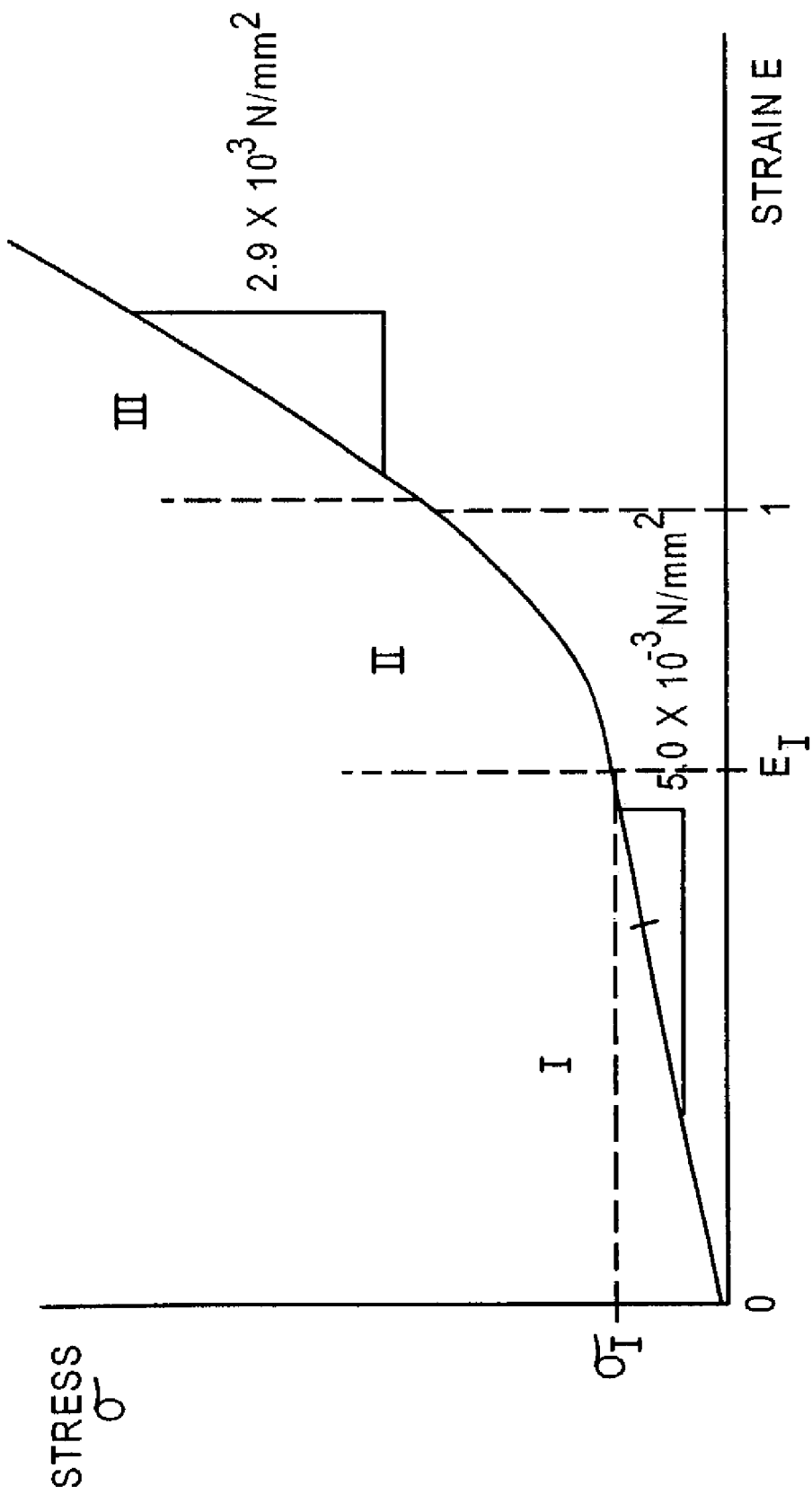
FIG. 4 shows strain characteristics for skin for differing degrees of applied stress.

FIG. 4 shows three regions of the skin's elastic modulus, i.e. the amount force (stress) required to deform the skin a given degree (strain). This curve is the result of the unique mechanical organization of the skin. This mechanical organization can be thought of as large numbers of loose collagen fibers connected together at randomly distributed nodal points. The mechanical behavior of such a system is very similar to that of a woven material such as a nylon stocking. As the material is stretched, the fibers are first straightened out and become oriented in the direction of the stress (shown in FIG. 4 region I). A relatively small amount of stress is required to produce this level of strain, with a modulus of elasticity typically $5 \times 10^{-3}$ N/mm². Skin is elastic over this range.

Generally at the end of region I and slightly into region II, the elasticity of the skin substantially decreases and the skin becomes taut. In region II, some fibers become fully aligned in the direction of the stress and then carry stress directly. Further deformation will result in ever-increasing numbers of collagen fibers being recruited to support the stress. The modulus of elasticity, or stiffness, of the skin increases rapidly as this process continues until it matches the stiffness of the collagen fibers themselves (region III). The modulus of elasticity in this region is typically $3 \times 10^3$ N/mm².

In the present invention, the desired differential motion applied to the skin should be of high enough amplitude to create pore opening forces, but low enough to minimize stretching of collagen fibers in the skin. Deformation should be limited to the area of region I and the low strain area of region II of FIG. 4, where the collagen fibers are not significantly stretched. To that end, the mechanical characteristics of the portions of the invention that contact the skin, called the contacting elements, and the amplitude of the moving contact elements must be such that the degree of stress on the skin does not exceed some value $\sigma_f$ thus keeping the amount of stain in the skin below the value $E_f$ of FIG. 4.

A first embodiment of the present invention is shown generally in FIG. 6, wherein movable skin contacting elements are located in the same plane as stationary skin contacting elements, and the bi-directional differential action is shear, i.e. the two elements move in parallel to each other along their length. The arrangement shown includes two skin contact elements 57 and 59 and a backing/spacer plate 61.

The movable and non-movable skin contacting elements are basically identical. In the embodiment shown, the individual contact elements 57 and 59 are each mounted on mounting plates. The fixed contact element 57 is mounted on mounting plate 58, while the oscillating contact element 59 is mounted on mounting plate 60. The contact elements are narrow and somewhat elongated and are shown in detail in FIG. 7 and 8. In the embodiment shown, the dimensions of the contact elements are typically 0.800 inches long and 0.09 inches wide. The edges of each contact element are beveled; giving it a somewhat rounded end face, while the respective ends are also rounded, as shown in the drawings.

Figure 8:
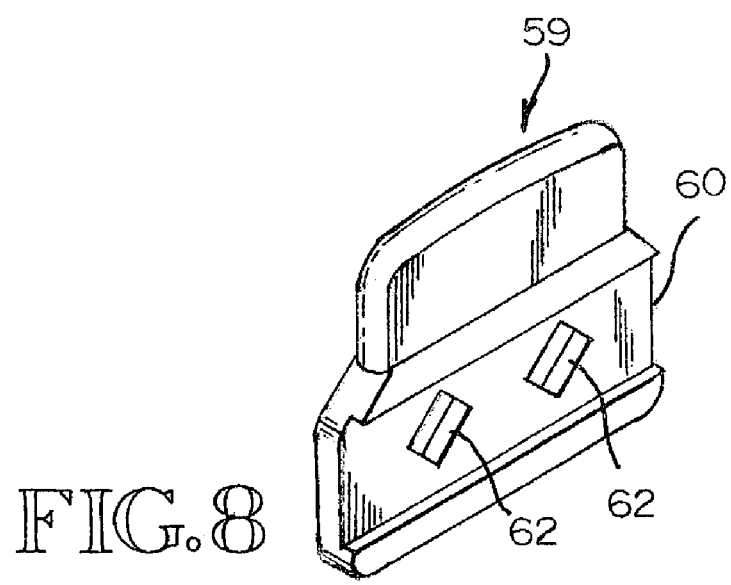
FIG. 8 is a schematic view of a movable contact element part of the apparatus of FIG. 6.

The mounting plate 58 for the fixed contact element is approximately 1.18 inches wide. The upper corners of mounting plate 58 are both cut off, at a 36° angle. The height of the mounting plate 58 is 1.4 inches. FIG. 8 shows the combination of contact element 59 and mounting plate 60 for the oscillating contact element. Mounting plate 60 is, in the embodiment shown, substantially rectangular, with a length of 1.0 inches and a height of 0.5 inches. The upper corners of mounting plate 60 are cut off, i.e. beveled, at an angle of 45°, while the lower corners are rounded.

Oscillating contact element 59 is mounted on mounting plate 60 on the upper edge thereof. The upper edge of contact element 59 is approximately 0.298 inches above the upper edge of mounting plate 60. Mounting plate 60 includes two drive openings 62-62 therethrough, so that the mounting plate 60 and contact element 59 can be moved back and forth by a driver mechanism discussed below. In the embodiment shown, the drive holes 62 are approximately square, 0.154 inches on each side.

The oscillating contact element 59 on its mounting plate 60 and the fixed contact element 57 on its mounting plate 58 are then positioned immediately adjacent to each other, as shown in FIG. 6. The two contact elements 57 and 59 are thus substantially in registry. The two assemblies are held together and attached to the driver mechanism 50 by two connecting screws 46-46. Hence the contact elements may be removed and replaced. The oscillating contact element assembly is movable by means of the driver that moves it reciprocally (back and forth), such that the mounting plate 60 moves parallel to mounting plate 58, and contact element 59 moves reciprocally in parallel with contact element 57.

The drive assembly shown generally at 50 includes two drive buttons 52-52 that move reciprocally a selected distance. These drive buttons extend into drive openings 62-62 on the oscillating mounting plate. The oscillating contact element in the embodiment shown has a frequency within the range of 20 Hz to 1 kHz, with a preferred value range of 80-200 Hz. As indicated above, the action of the drive assembly moves the mounting plate 60 parallel with mounting plate 58, so that the oscillating contact element 59 moves parallel to the length of the adjacent fixed contact element 57. In the embodiment shown, the contact element and the mounting plates are made from stainless steel, although the contact elements could also be coated with a compliant material or be composed entirely of compliant material, such as shown at 63 in FIG. 14, or the contact elements could be replaced by bristle brush tufts or the like.

In the embodiment shown, a center-to-center distance of approximately 0.125 inches results in a separation between 0.09 inches wide contact elements 57 and 59 of approximately 0.035 inches. Contact element 59 moves reciprocally over a total distance in a range of 0.02 inches or 0.08 inches, with a preferred value of approximately 0.040 inches (+/− 0.020 inches from its neutral position to its peak position) along contact element 57. The surface finish of the contact elements 57 and 59 is such that the skin primarily moves in contact with the contact elements. A surface roughness range of 5 to 20 microinches is effective, with a preferred value of 10 microinches. The surfaces must be sufficiently rough that the motion of the contact elements is transferred to the skin with minimal or no slippage. If the surface is too smooth, the skin could be abraded. The contact element could be an elastomer or a closed cell foam. It could be a knobby surface or even fingers.

In operation of the embodiment of FIG. 6, the edge faces of the contact elements will be positioned lightly against the skin surface and the device activated by a switch. The contact element 59 begins to oscillate. The device is then moved at a slow rate across the skin surface, for instance two centimeters per second. The device operates with a ratio of peak amplitude to the space (distance) between adjacent skin contacting elements of typically 0.57. With that action, shear forces are applied to the skin, with sufficient amplitude to slightly distort the skin and force open the pores, but low enough to minimize any skin stretching.

At the above-noted frequency range, with a minimum of 20 Hz, each pore opening is deformed approximately 10 times per second. At higher frequencies, the number of deformations per second would be proportionately greater.

Alternating shear stress in the tissue surrounding the infundibulum is produced, with the adhesion between the sebaceous plug and the infundibular wall being weakened or significantly reduced, so that the plug is essentially loosened in the pore.

While the embodiment of FIG. 6 shows one fixed contact element and one movable contact element, it should be recognized that a plurality of fixed contact elements and oscillating contact elements could be used to provide a wider coverage for the device. In the case of a plurality of contact elements, the movable multiple contact element(s) are interdigitated with the fixed contact element(s) and are driven in a ganged manner.

In addition, both contact elements can be driven, preferably in equal and opposite directions of motion with respect to each other. A peak amplitude of 0.02 inches for each of two moving elements would result in a peak amplitude of relative motion of 0.04 inch.

Figure 7:
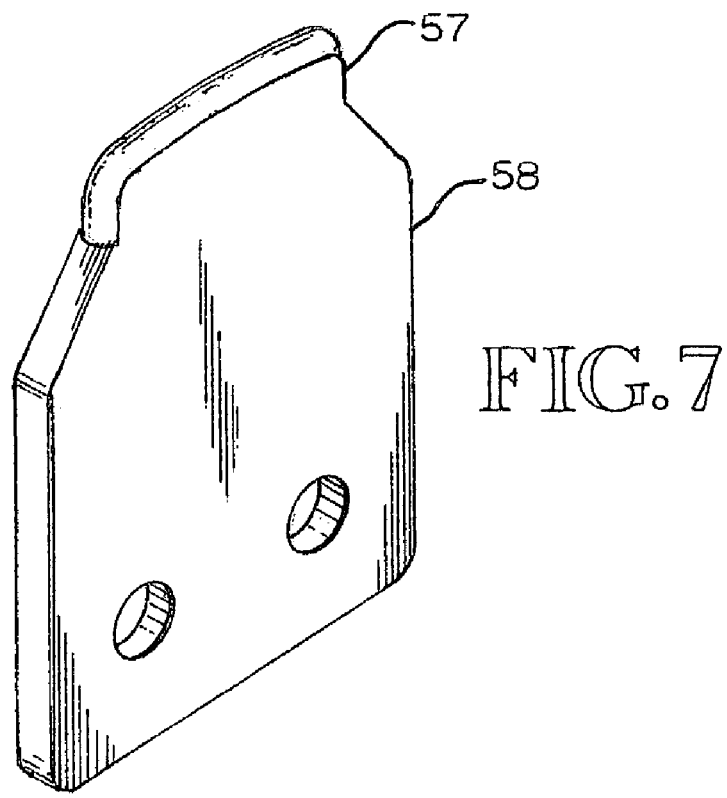
FIG. 7 is a schematic view of a fixed contact element part of the apparatus of FIG. 6.
Figure 9A:
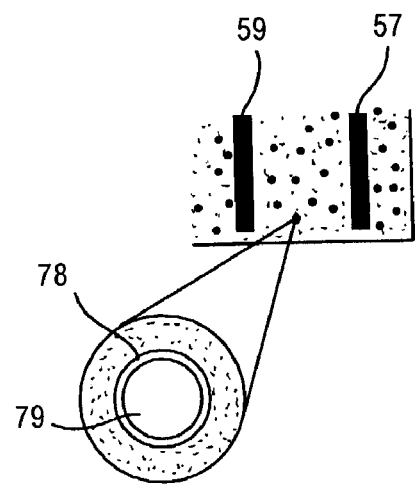
FIGS. 9A, 9B, 9C and 9D show the effect on a typical sebaceous plug positioned within a skin pore subjected to the action of the apparatus of FIG. 6.
Figure 9B:
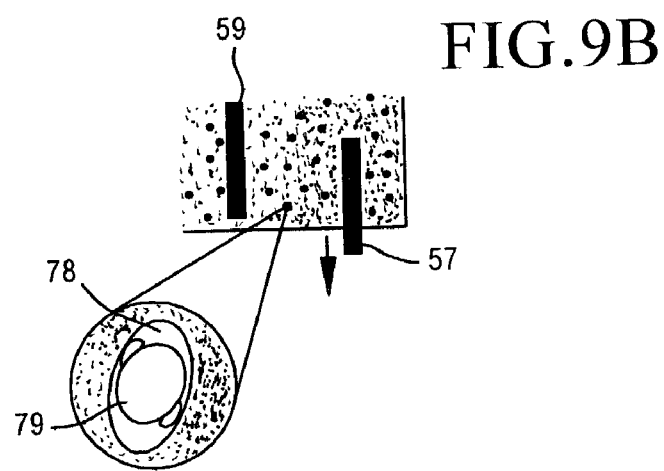
Figure 9C:
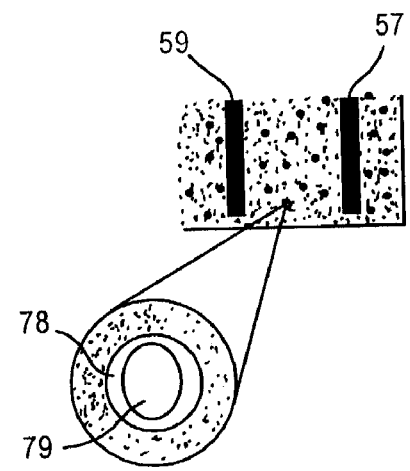
Figure 9D:
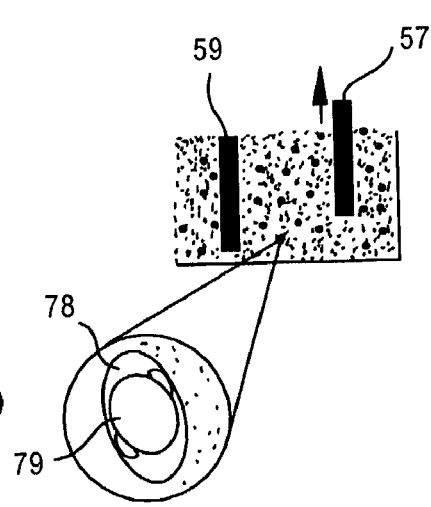

FIGS. 9A-9D show the action on the skin and a sebaceous plug with the shear embodiment of FIGS. 6-8. FIG. 9A shows a pore 78 blocked by a sebaceous plug 79 therein. The contact elements are in a neutral position. The movable contact element will then be moved in one direction, in parallel with the fixed contact element, which distorts the sebaceous plug (FIG. 9B). The movable contact element and mounting plate combination is then reversed and returns to the neutral position. This is shown in FIG. 9C. The movable contact element continues in the opposite direction, which deforms the sebaceous plug in the opposite direction (FIG. 9D). This is accomplished at the specified frequency. While generally this "double" motion is preferred, it is possible to move the movable contact in one direction only relative to the neutral/rest position. Continued respective action dislodges or releases the sebaceous plug from the pore walls. The device is slowly moved across the surface of the skin, producing the above results over an entire skin area.

Figure 10:
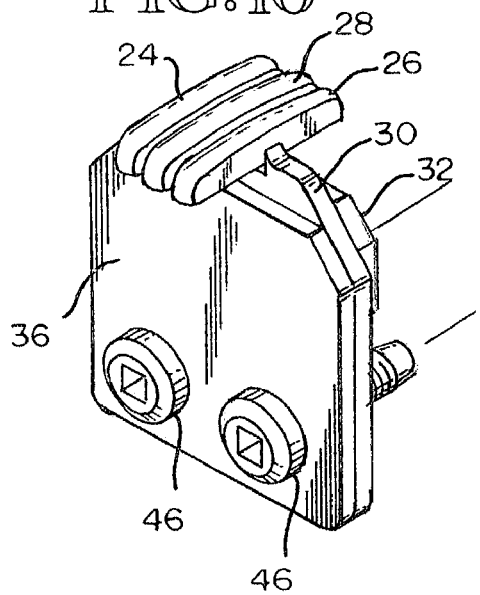
FIG. 10 is a schematic view of a variation of the mechanical device of FIG. 6.
Figure 11:
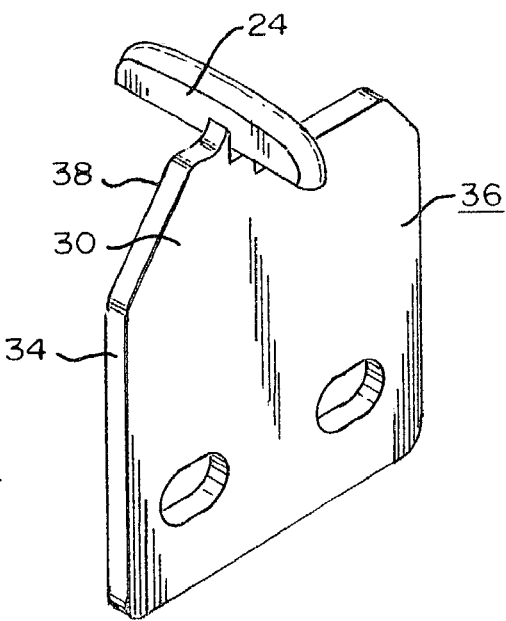
FIG. 11 is a schematic view of a fixed contact element part of the apparatus of FIG. 10.
Figure 12:
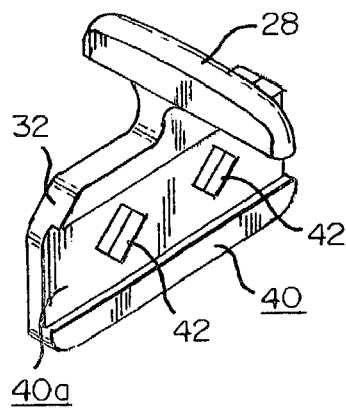
FIG. 12 is a schematic view of a movable contact element part of the apparatus of FIG. 10.

An alternative mechanical arrangement is shown in FIGS. 10-12. It includes two fixed skin contact elements 24 and 26 and an intermediate oscillating contact element 28. The configuration of the elements in the tension/compression arrangement is similar to that of the elements of the embodiment of FIGS. 6-8, although the "shear" action of the embodiment of FIGS. 6-8 is generally preferred. In both embodiments, the differential strain on the skin produced by the mechanical action is sufficient to result in a breaking away of the plug from the skin, due to the difference in elasticity between the plug material and the skin.

In the embodiment of FIGS. 10-12, the individual contact elements 24, 26 and 28 are each mounted on mounting plates. The fixed contact elements 24, 26 are mounted on mounting plates 30-30 (FIG. 11), while the oscillating contact element 28 is mounted on mounting plate 32 (FIG. 12). The contact elements are narrow and somewhat elongated and are shown in detail in FIGS. 11 and 12. In the embodiment shown, the contact elements are typically approximately 0.800 inches long and approximately 0.090 inches thick. The edges of each contact element are beveled; giving each contact element a somewhat rounded end face, while the respective ends are also rounded, as shown in the drawings. The mounting plate 30 for the fixed contact element is approximately 1.18 inches wide. The upper corners of mounting plate 30 are both cut off, at a 36° angle. The height of the contact element is somewhat less (1.25 inches) on one side of the contact element relative to the other side (1.4 inches).

In the embodiment shown, the fixed contact elements 24, 26 are mounted cross-wise (perpendicular) to the mounting plate, approximately 0.5 inches from one edge 34 thereof. The fixed contact elements are offset laterally, such that they extend approximately 0.316 inches from one surface 36 of mounting plate 30, and approximately 0.406 inches from the opposing surface 38.

FIG. 12 shows the combination of contact element 28 and mounting plate 32 for the oscillating contact element. Mounting plate 32 is, in the embodiment shown, substantially rectangular, with a length of 1.0 inches and a height of 0.5 inches. The upper corners of mounting plate 32 are cut off, i.e. beveled, at an angle of 45°, while the lower corners are rounded.

Oscillating contact element 28 is mounted perpendicularly to mounting plate 32 on the upper edge thereof. The upper edge of contact element 28 is approximately 0.298 inches above the upper edge of mounting plate 32 and is offset, so that it extends approximately 0.472 inches from surface 40 of mounting plate 32. Mounting plate 32 includes two drive holes 42-42 therethrough; so that the mounting plate 32 and contact element 28 can be moved back and forth by a driver mechanism discussed below. In the embodiment shown, the drive holes 42 are approximately square, 0.154 inches on each side.

The oscillating contact element 28 on its mounting plate 32 and the fixed contact elements 24 and 26 on their mounting plates 30 are then positioned immediately adjacent to each other, with the two fixed contact element assemblies being back-to-back, but reversed, as shown in FIG. 10. The three contact elements 24, 26 and 28 are thus substantially in registry. The three assemblies are held together and attached to the driver by two connecting screws 46-46. The oscillating contact element assembly is movable by means of a driver that moves it back and forth, such that the mounting plate 32 moves parallel to mounting plates 30, and contact element 28 moves alternately toward and away from contact elements 24 and 26.

A drive assembly similar to that shown at 50 in FIG. 6 includes two drive buttons which move back and forth a selected distance. These drive buttons connect to the drive holes 42-42 on the oscillating mounting plate 32. The oscillating contact element in the embodiment shown moves at a frequency within the range of 20 Hz to 1 kHz, with a preferred range of 80-200 Hz. As indicated above, the action of the drive assembly moves the mounting plate 32 parallel with mounting plates 30, so that the oscillating contact element 28 moves toward (or away from) one adjacent fixed contact element 24 and away from (toward) the other adjacent fixed contact element 26.

In the embodiment shown, contact elements 24 and 26 are separated by a center-to-center distance of approximately 0.280 inches and contact element 28 moves reciprocally over a peak-to-peak distance of approximately 0.150 inches between contact elements 24 and 26. Movement between a neutral/rest position and a peak distance (one direction) and back to neutral is also possible. In operation of the embodiment of FIGS. 10-12, the edge faces of the contact elements will be positioned lightly against the skin surface and the device activated by a switch. The contact element 28 begins to oscillate. The device is then moved at a slow rate across the skin surface, for instance two centimeters per second. With that action, shear forces of tension and compression are applied to the skin, with sufficient amplitude to slightly force open the pores, but low enough to minimize any skin stretching or deformation. In this embodiment, the peak amplitude of motion is approximately 39% of the spacing between adjacent contact elements.

At the above-noted frequency range, with a minimum of 20 Hz, each pore opening is deformed approximately 10 times per second. At higher frequencies, the number of deformations per second would be proportionately greater. Alternating tension and compression stress in the tissue surrounding the infundibulum results, with the adhesion between the sebaceous plug and the infundibular wall being weakened or significantly reduced, so that the plug becomes essentially loose in the pore.

While the embodiment of FIGS. 10-12 shows two fixed contact elements and one movable contact, it should be recognized that only one fixed contact element could be used, or a plurality of fixed contact elements and oscillating contact elements can be used to provide a slightly wider coverage. In the case of a plurality of contact elements, the moving multiple contact element(s) are interdigitated with the fixed contact element(s), and are driven in a ganged manner.

In addition, both contact elements can be driven, preferably in equal and opposite directions of motion with respect to each other. A peak amplitude of 0.02 inches for each of two moving elements would result in a peak amplitude of relative motion of 0.04 inches.

FIGS. 13A-13D show action on a pore with a sebaceous plug with the tension/compression arrangement of FIGS. 10-12.

FIG. 13A shows a pore 78 blocked by a sebaceous plug 79 therein. The contact elements are in a neutral position. The movable contact element will then be moved in one direction, perpendicularly away from the fixed element, which deforms the sebaceous plug and causes deformation of the pore in one direction (FIG. 13B). The motion is then reversed and returns to the neutral position, relaxing the force between the sebaceous plug and the acroinfundibulum, as shown in FIG. 13C. The movable contact element will then be moved in the opposite direction, perpendicularly away from the fixed element, which also deforms the sebaceous plug opposite direction (FIG. 13D). This sequence is accomplished at a frequency within the range of 20-1,000 Hz, and preferably in the range of 80-200 Hz. Continued action dislodges or releases the sebaceous plug from the pore walls. The user slowly moves the device across the surface of the skin, producing the above results over an entire skin area.

A further alternate mechanical configuration is shown in FIGS. 15-22. These configurations operate on substantially the same principles as the device described above, but have contact elements composed of bristle tufts. In these embodiments, the base portions holding the bristle tufts are analogous to the mounting plates described above. Instead of rigid or compliant solid contact elements, a plurality of bristle tufts are employed. Each tuft is further composed of a plurality of filaments or bristles. The bristles may be made from any material suitable for the application, with the preferred material being Nylon 612. The diameter of each bristle is in the range of 2 to 5 mile with a preferred diameter of 3 mils, and of lengths in the range 0.25 to 0.60 inches, with a preferred length of 0.43 inches in length.

The base of the tuft has a diameter in the range of 40 to 100 mils with a preferred diameter of 60 mils for the tufts of the fixed and moving interior bristle tuft rows and a preferred diameter of 80 mils for the fixed exterior bristle tuft row. The diameter and length of the bristles determine their stiffness. Using the same material, larger diameter bristles are stiffer than smaller diameter bristles. Generally longer bristles are softer than shorter bristles. The material used to make the bristles also dictates the stiffness character of the bristles. Additionally, the rows can be made with individual tufts having a different number of bristles. Generally, having more bristles of a smaller diameter in a tuft will produce a softer sensation.

Tufts of 0.003 inches diameter Nylone 612 bristles 0.43 inches in length product a lateral stiffness which works well in moving the skin within Region I and the lower part of Region II of FIG. 4. Such tufts produce a lateral spring constant of approximately 10 grams/inch at a displacement of 0.06"; i.e. a lateral displacement of 0.06" of the end of a tuft results when a lateral force of 0.6 grams is applied to the end of the tuft relative to the base.

FIGS. 15-18 show an embodiment using linear motion of the bristle rows. In FIGS. 15-16, both sets of bristle rows (first set of three rows 70-70, second set of three rows 72-72) move with respect to each other, while in FIGS. 17-18, one set of four rows 82-82 is fixed and the other set of three rows 80-80 moves. In both embodiments, the rows of moving/fixed bristle tufts are surrounded by a circle of bristle tufts 84, the circle of bristles 84 being fixed and functioning like a curtain to keep cleanser/water on the skin.

Figure 19:
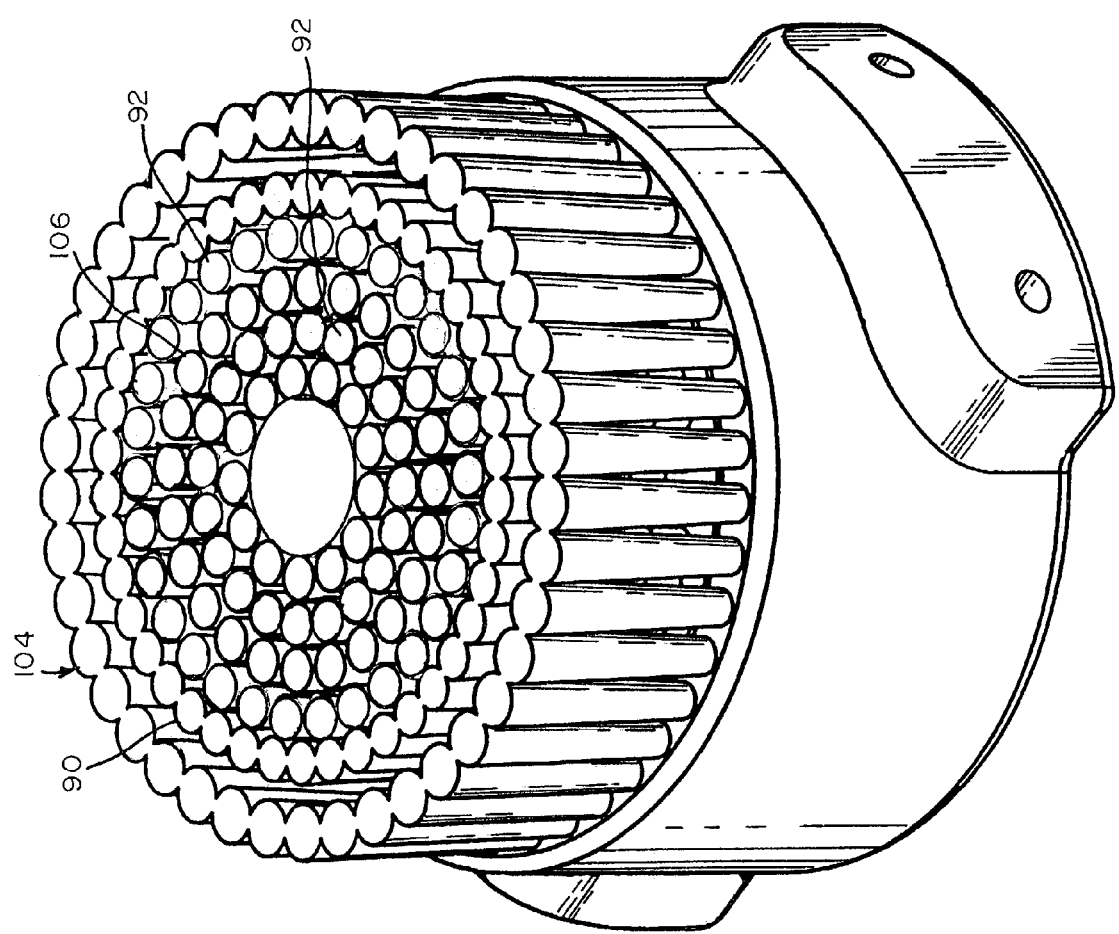
FIG. 19 is a diagram showing a further alternate embodiment of the present invention with alternately rotationally movable sets of bristle tufts.
Figure 20:
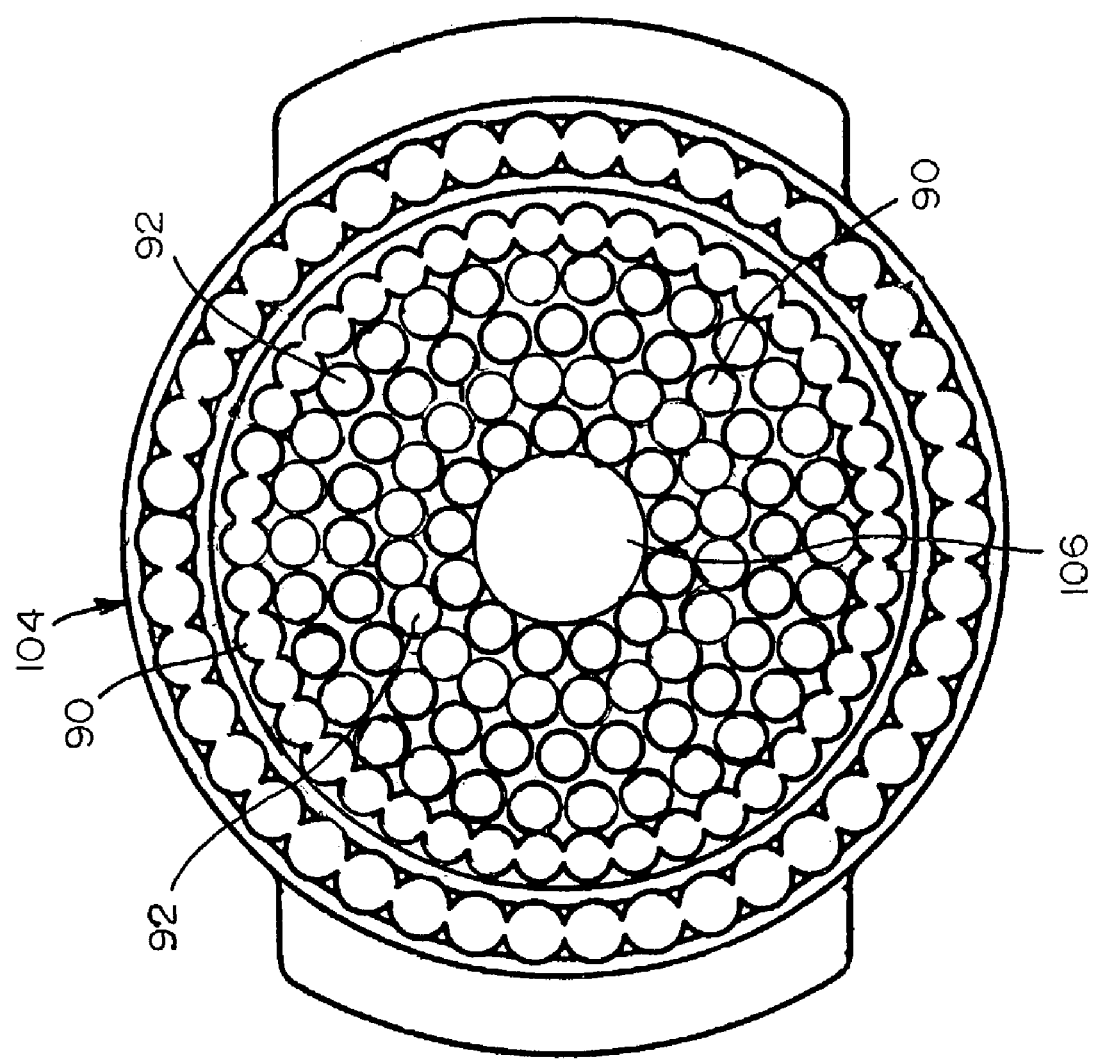
FIG. 20 is a top view of the mechanical device shown in FIG. 19.
Figure 21:
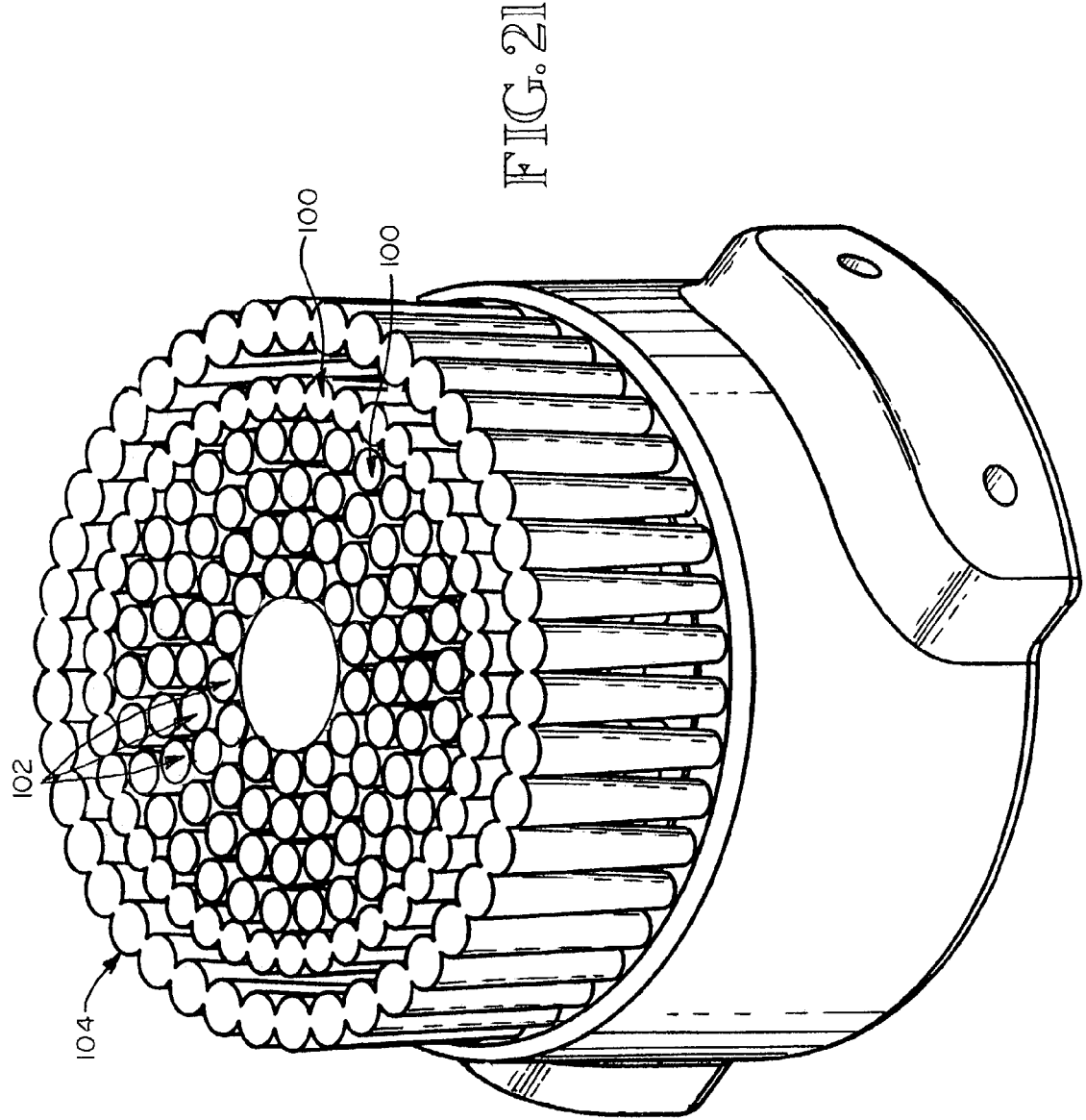
FIG. 21 is a diagram showing a variation of the mechanical device shown in FIG. 16 with a single set (two rows) of rotationally moving bristle tufts.
Figure 22:
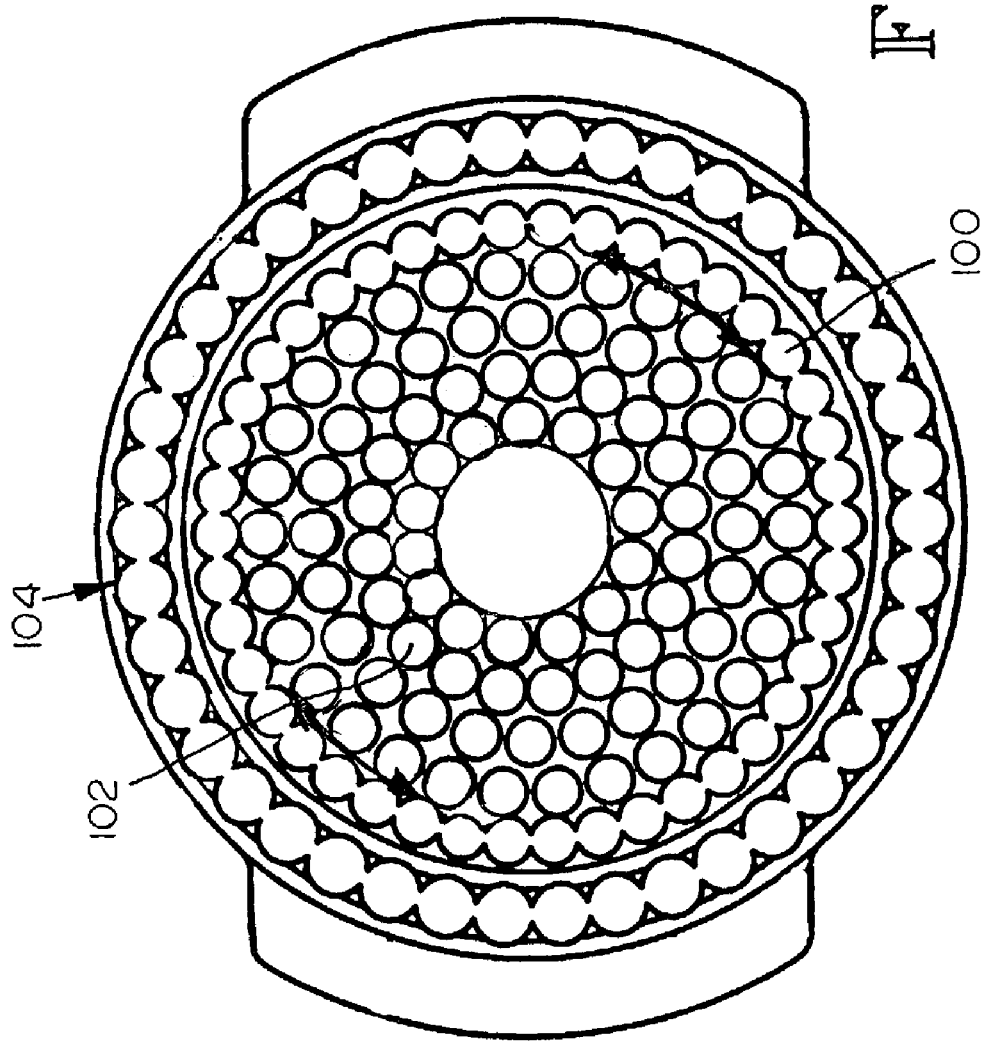
FIG. 22 is a top view of the mechanical device shown in FIG. 21.

In another embodiment shown in FIGS. 19-22, the row(s) of bristle tufts are circular and move in an arcuate manner with the axis of rotation perpendicular to the surface of the skin. FIGS. 19-20 show an embodiment in which both sets of circular bristle rows (two rows 90-90 and two rows 92-92) move with respect to each other, while FIGS. 21-22 show an embodiment in which one set of two rows 100-100 moves and the other set of three rows 102-102 is fixed. In each case, one row each of 90 and 92 bristle rows and one row each of 100 and 102 bristle rows would likely be sufficient for cleansing action. Additional rows beyond that shown could also work. In both of these embodiments, the rows of bristles are encircled by a circle of fixed bristles 104, acting as a curtain for liquid, etc. In the embodiment of FIGS. 19 and 20, there is also a circle of fixed bristles 106 inside of the circle of rows 90 and 92.

The adjacent rows of bristle tufts for the devices shown in FIGS. 15-22 more relative to each other at an amplitude sufficient to deform the skin in region I and slightly into region II of FIG. 4 as shown to produce the cleansing action.

Figure 5B:
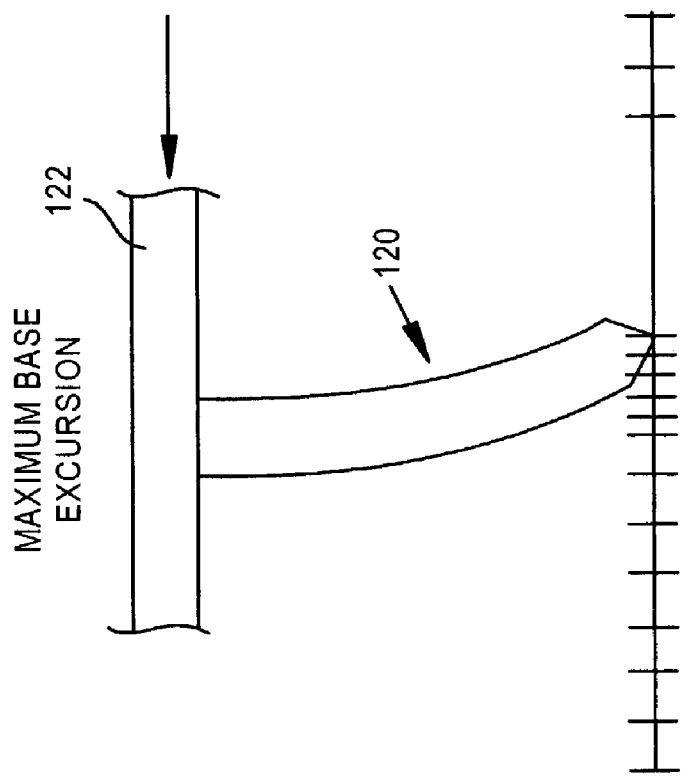
FIGS. 5A and 5B show the relative displacement of a single tuft of bristles moving against the skin.
Figure 5A:
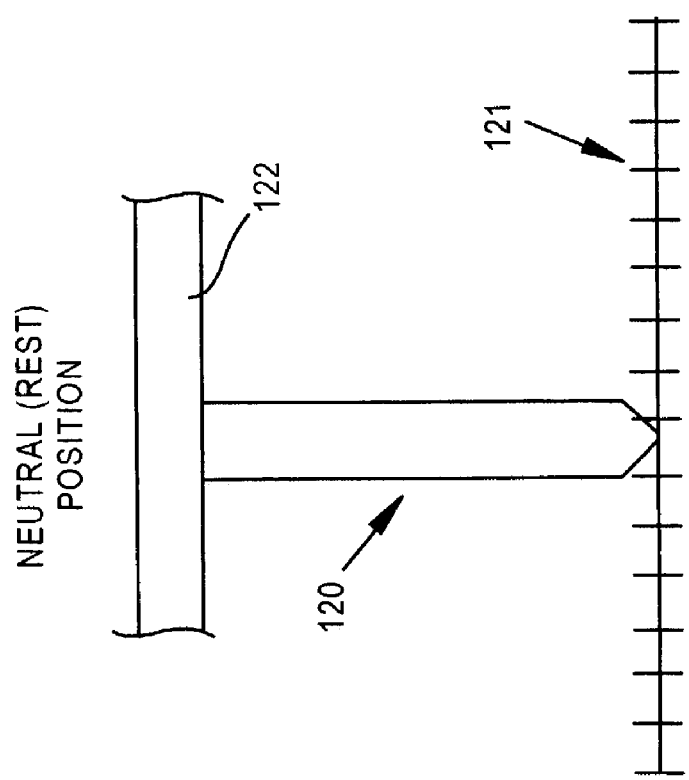

FIG. 5A shows the cleansing action of bristles with a single tuft of bristles 120 against the skin 121 when base 122 is at rest (neutral), while FIG. 5B shows the tuft 120 when the base 122 is at a maximum excursion. The skin 121 is indicated with "tick" marks on a horizontal line, with the tick spacing showing relative deformation of the skin.

In FIG. 5A, the uniform spacing of the tick marks indicates that there is no deformation of the skin when the bristles are in the rest position. FIG. 5B shows that the skin has been compressed slightly by the bristles in the direction of motion of the base, and stretched slightly behind the tips of the bristles. In typical operation, both the bristles and the skin deform, and there is relatively little slippage of the bristles on the skin. As the tuft base moves from its rest (neutral) position, the skin deformation increases, as does its modulus, until the restorative force of the skin just balances that of the bristles.

Typical peak-to-peak amplitudes measured at the base of the bristle tufts of 0.05 inches to 0.25 inches can be used with rows having center-to-center spacing of 0.10-0.25 inches. This results in the peak amplitude (50% of peak-to-peak amplitude) of typically 40%, and in a range of 10% to 100% of the center-to-center spacing between adjacent rows of tufts. At high amplitudes, the bristles may also slide across the surface, especially if the brush is used with lubricating elements.

Referring now again to FIGS. 19-22, lubricating fluid can be supplied by the device, for example, through a central port 106 shown in FIGS. 19 and 20. Centripetal force tends to spread the emitted fluid onto the bristles, supplying relatively uniform wetting. The fluid is contained by the bristle curtain 104.

In the case of rotational configurations such as shown in FIGS. 19-22, the linear amplitude of motion is larger for the outer rings. The center-to-center spacing can be adjusted among the rows to maintain an approximately constant ratio of amplitude to inter-element spacing.

The bristle rows described above can also be replaced with flexible members, such as an elastomer or closed cell foam.

It is also possible to combine the advantages of the differential shear mode and tension/compression modes described above into a compound motion, for example, elliptical.

It is also possible to apply bi-directional motion to the skin via a single set of contact elements for cleaning or clearing the infundibular opening. Unlike the cases above in which there is a differential reciprocating motion between adjacent contact elements, the use of a single set of elements relies on inertia of the skin to effect a differential force on the pore openings. The single set of moving contact elements, such as a row of bristles, forces the skin immediately adjacent to it to move. This movement is coupled to skin regions somewhat distant through the skin's elasticity. However, skin also has inertia which resists motion, thereby producing a shear force in the direction of movement. This shear force decreases at greater distances from the moving contact elements.

Applying bi-directional reciprocating movement via a single set of contact elements is generally not as effective as using adjacent contact elements arranged to apply tension/compression or shear between them.

Figure 18:
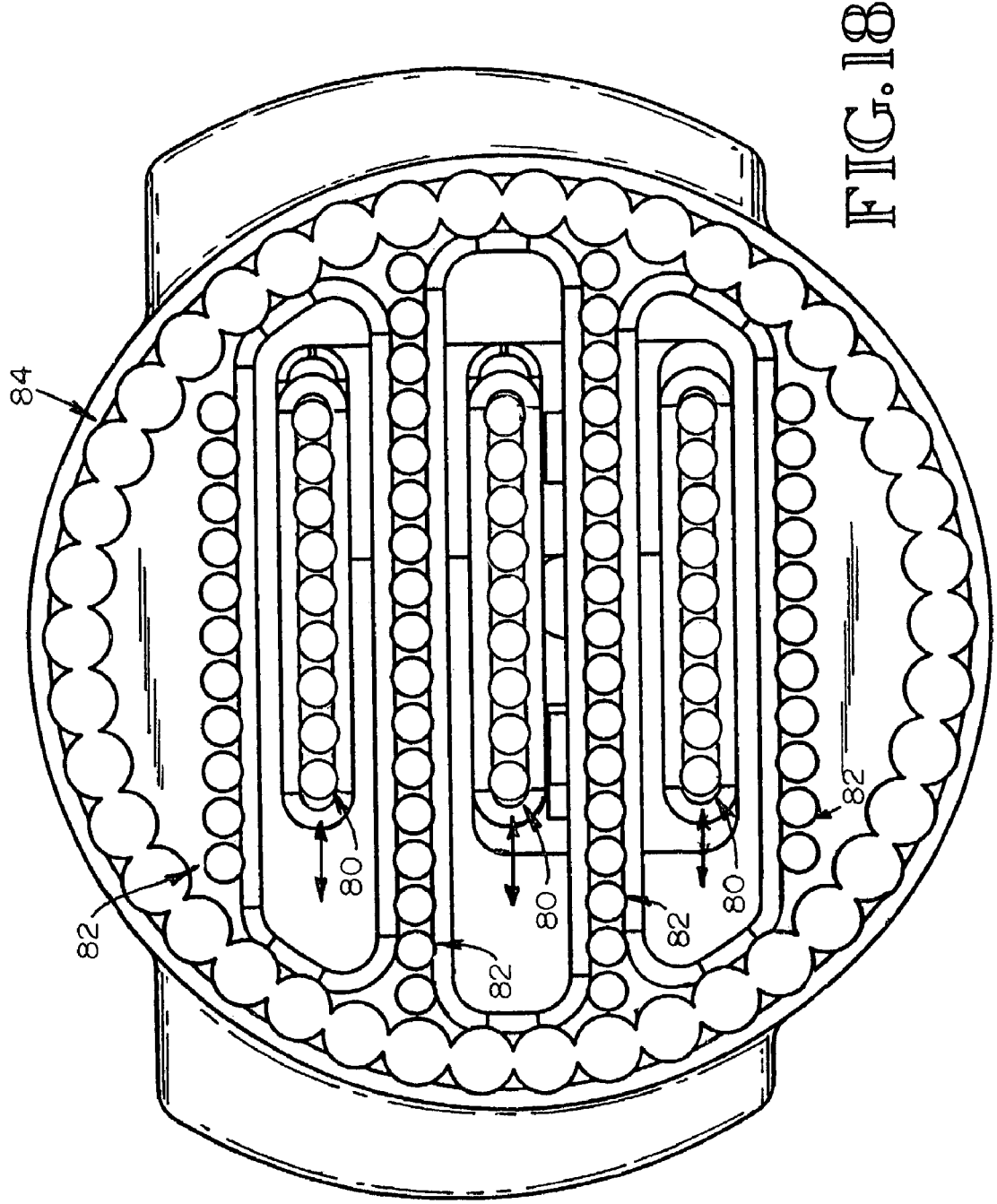
FIG. 18 is a top view of the device shown in FIG. 17.

The single set of reciprocating contact elements can be implemented in a linear manner, such as the device of FIGS. 17 and 18, with all linear bristles moving in unison. This single set reciprocating motion can also be implemented in an arcuate manner, such as the device of FIGS. 21-22, with all rows of bristles moving in unison. Where the contacting element comprises rigid or compliant material, the peak-to-peak amplitude of movement will be within the range of 0.04-0.150 inches, preferably 0.09 inches; if the contacting element is a row of bristles, the peak-to-peak amplitude of movement is within the range of 0.020 to 0.160 inches, preferably 0.082 inches.

Figure 23:
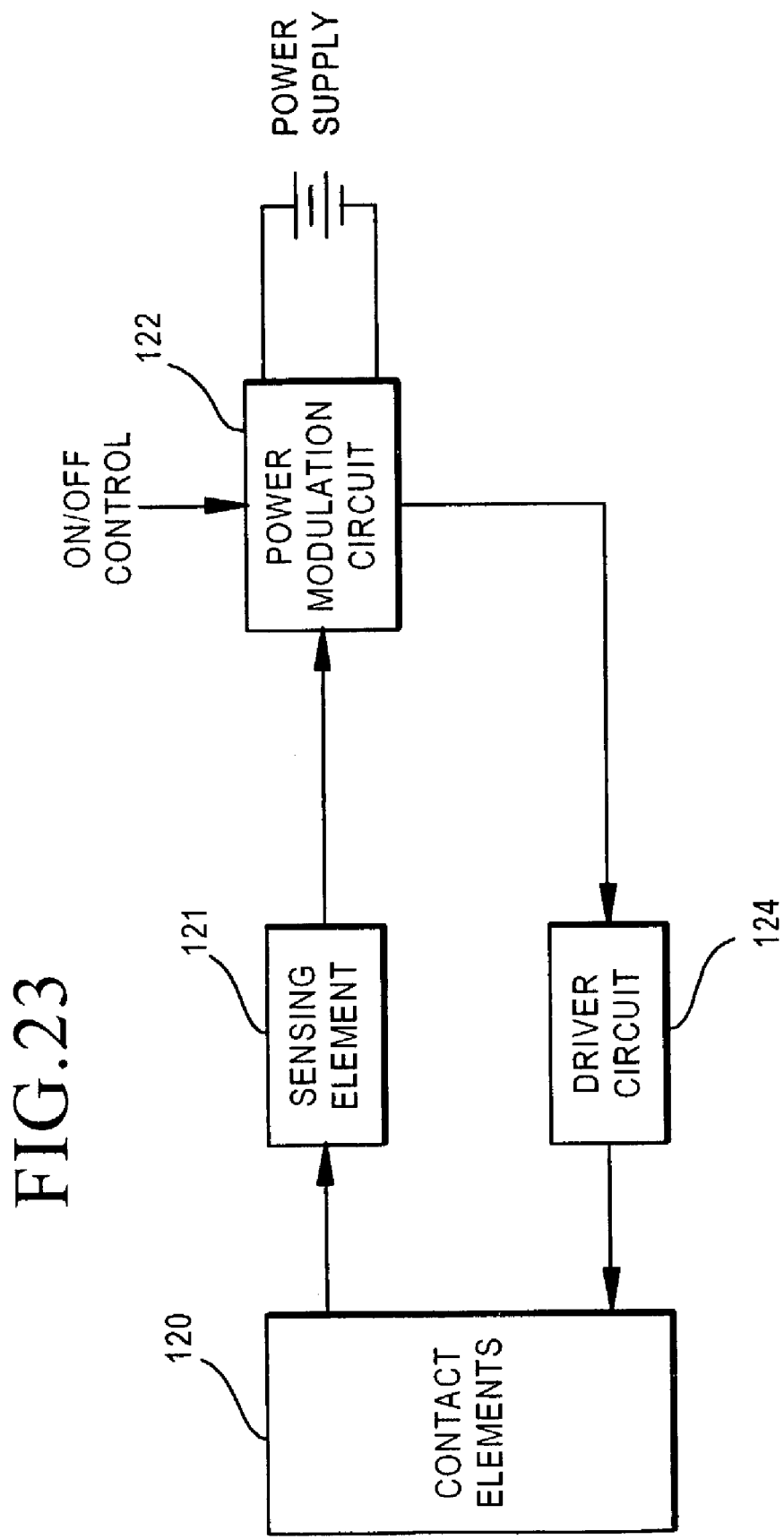
FIG. 23 is a schematic block diagram showing the control means for controlling the amplitude of motion as a function of pressure applied to the skin.

FIG. 23 shows a schematic block diagram for a control means for controlling the amplitude of the moving portions of the contact elements 120. The control means is composed of a sensing element 121, a power modulation circuit 122, and a driver circuit 124. The sensing element 121 senses the amount of pressure applied to the skin by the contact elements 120 and applies a signal to the power modulation circuit 122. The power modulation circuit 122 uses said signal to modulate the power of the driver circuit 124 and amplitude of the contact elements 120.

The control means operates in a plurality of operating modes with a preferred number of three operating modes. Proper operation of the apparatus requires that the pressure applied to the skin by the applicator remains in given range.

When pressure applied by the contact elements to the skin is below the lower threshold for proper operation of the apparatus, the amplitude of the applicator with the contact elements is substantially reduced from its nominal amplitude. This reduces the likelihood of splashing of fluids or cleaning agents when the applicator is not in contact with the skin.

When pressure applied by the applicator to the skin is above the lower threshold for proper operation of the apparatus, but below the upper threshold, the applicator is driven at nominal amplitude.

When pressure applied to the skin by the applicator is above the upper threshold for proper operation the amplitude of the applicator with the contact elements is substantially reduced from its normal amplitude or, preferably, stopped altogether. An alternative is to interrupt the power to the contact elements at a low frequency, for example 2-10 Hz, in order to create an audible or tactile feedback to the user to reduce the pressure. This excess pressure feedback signal reduces the likelihood that the applicator will cause too much motion of the skin.

The above-described control means provides not only safety and convenience, but also provides feedback to the user to maintain applicator pressure in the range for proper operation of the apparatus.

Figure 24:
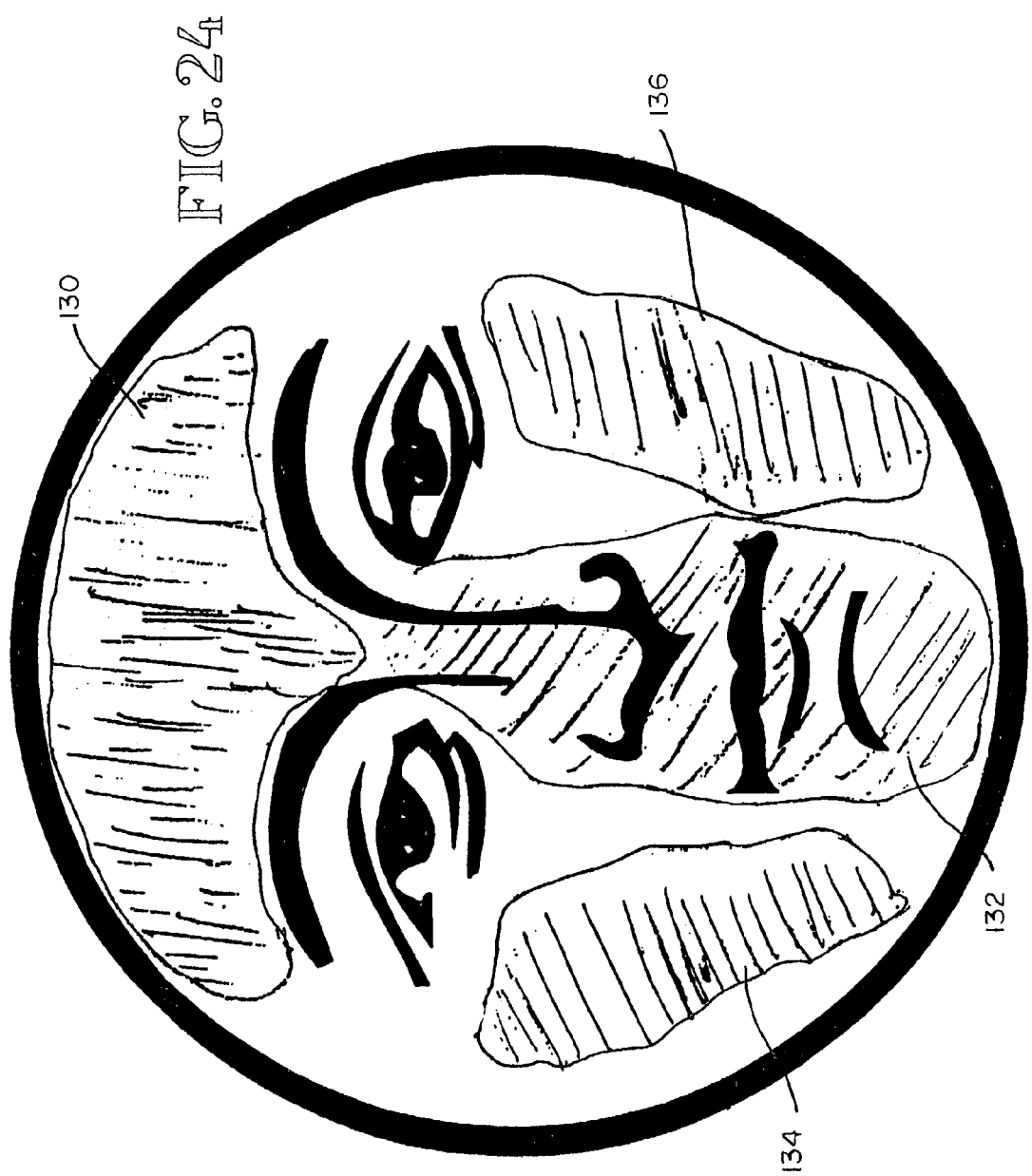
FIG. 24 is a schematic representation of the human face showing the various regions of the face that differ in the degree of sebum secretion and incidence of acne lesions.

FIG. 24 shows four regions of the face that differ in topology and degree of sebaceous secretion. Generally the face is divided into two distinct regions, the so-called "T-zone" 130 and 132, and the outer cheek areas 134, 136. The T-zone is the part of the face consisting of the forehead, nose and the area around the mouth, including the chin. It is so named because it is shaped like the letter T.

Often the T-zone is more prone to acne, as the percentage of sebum glands in this area tends to be higher than on the outer cheeks. An important component of the present invention, therefore, is a timer means to assist the user in properly treating the differing zones of the face, according to the typical incidence of acne in that area, without over- or under-treating the area. The total treatment time may be from 30 seconds to two minutes and preferably one minute. Further, the total time may be subdivided into two or more and preferably four time periods. In the present invention, the first time period is 20 seconds for treatment of the forehead 130; the second time period is 20 seconds for treatment of the nose, perioral area and chin 132; and 10 seconds for each outer cheek areas 134, 136.

Figure 25:
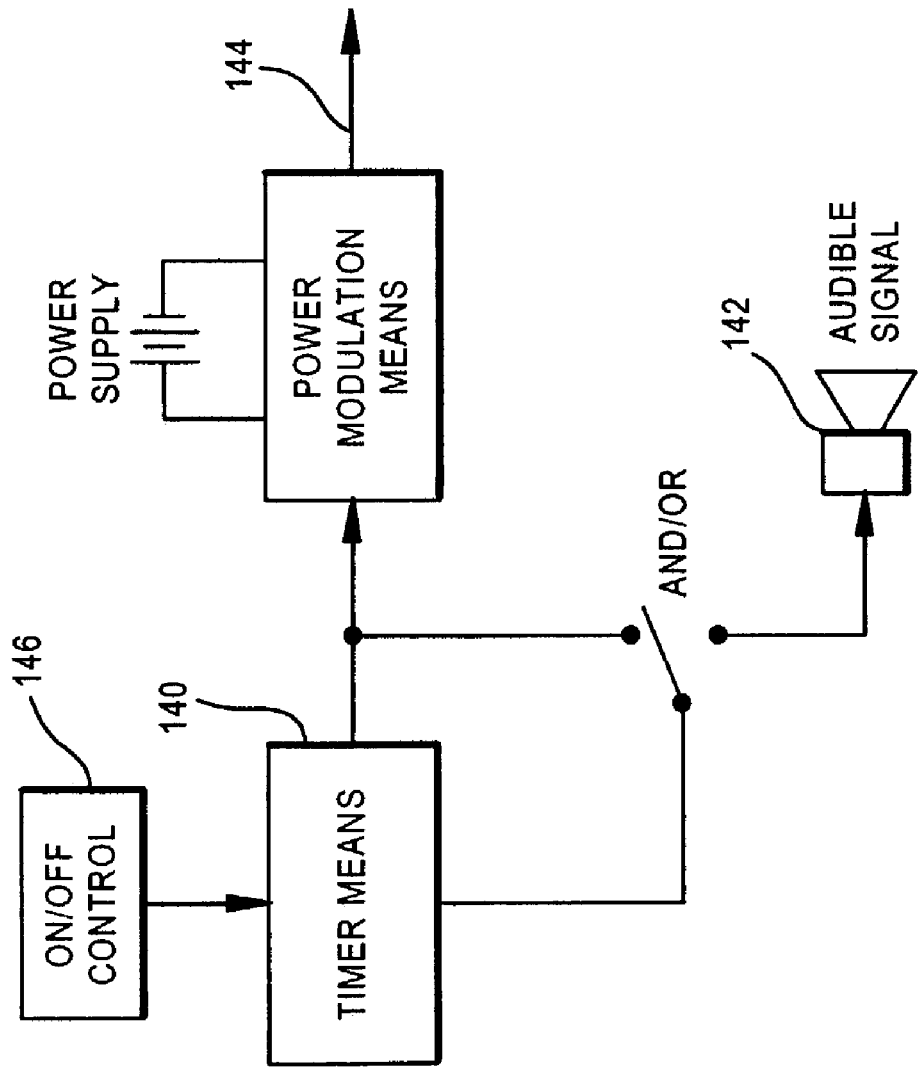
FIG. 25 is a block diagram of a timer structure useful with the present invention.

A timer means 140 (FIG. 25) prompts the user by providing either an audible signal 142 or a detectable change in the motion of the moving contacting element, or both simultaneously. This prompt instructs the user when the preferred treatment time has elapsed for each area of the face. The timer can be enabled or disabled after the apparatus is turned on, by means of an on/off switch 146 being pressed on for a selected period of time. A first audible signal can be used to indicate that the timer has been enabled and a second audible signal to indicate that the timer has been disabled.

In summary, applying differential motion locally to the infundibular (pore) opening results in the clearing of sebaceous plugs from the acroinfundibulum (top of the pore). The differential motion, whether linear, arcuate or elliptical, applies forces to the interface between the comedone (sebaceous plug) and the surrounding tissue, thus breaking the adhesion between the acroinfundibular wall and the sebaceous plug.

A bi-directional, return-to-center motion generally provides better cleaning than unidirectional motion due to the nature of the sebaceous plug, i.e. the sebaceous plug can be thought of as a generally disorganized matrix of flat, brick-like corneocytes embedded in a "mortar" of oxidized sebum lipids. Adhesion of the plug to the wall of the acroinfundibulum is thought to be caused by a combination of oxidized sebum and ceramide lipids. Because the orientation of the corneocytes is not completely random relative to the wall of the acroinfundibulum, it is possible that unidirectional motion alone would eliminate some of the adhesion but may be insufficient to loosen the sebum plug. The preferred embodiment of the invention applies bi-directional motion such that most or all of the corneocytes are subject to adhesion-breaking stresses irrespective of their orientation.

Limiting the amplitude of bi-directional motion to an extent which generally maintains the skin in a region of low strain is also beneficial. High amplitude bi-directional or uni-directional motion places the collagen fibers in a higher strain condition.

In use, our invention applies cyclic deformation and relaxation many times per second to the skin surrounding the acroinfundibulum and any sebaceous plug. The repetition of differential vibratory cycles supplies a therapeutic effect by gradually breaking the adhesion between the acroinfundibulum and the sebaceous plug.

The present invention is intended to operate in a frequency range of 20-1,000 Hz. A preferred range is 80-200 Hz. Below 80 Hz, the vibration rate is less than optimal and the mechanical implementation is more difficult. Above 200 Hz, a strong tickle reaction, usually unpleasant, occurs in the nose region. Assuming a 1 cm width of active surface of the device operating at the minimum frequency, moving the device across the skin surface linearly at 2 cm/sec would result in each pore experiencing 10 deformation cycles, many more times than would be practicable by any manual technique. At higher frequencies the number of deformations per stroke of the appliance would be proportionally greater.

There are two basic modes of differential movement that can be applied: shear and tension/compression. The shear mode device applies a linear differential motion via narrow elements which contact the skin, and which move in the direction of their length with respect to each other. The device typically applies a sinusoidal oscillation to adjacent contact elements. The arrangement includes two contact element assemblies. The device moves the contact elements in parallel to each other along their long axis. Sufficient frictional forces between the surface of the contact elements and the skin surface will transfer this motion to the skin, creating a shear action on the skin between them as shown in FIGS. 9A-9D.

The tension/compression mode device, in contrast to shear mode, moves the contact elements toward and away from each other. The oscillations are perpendicular to the long axis of the contact elements (i.e. one element moving toward one neighbor and away from its other neighbor), thus creating alternating tension and compression stress in the tissue surrounding the infundibulum. Sufficient frictional forces between the surface of the contact elements and the skin surface will transfer this motion to the skin as shown in FIGS. 13A-13D.

Alternatively to one contact element moving, both contact elements may move with respect to the device body, and counter to one another.

The skin contacting elements can be rigid or flexible. Rigid surfaces can be made from stainless steel and plastic. Flexible contacting surfaces can include bristles, elastomers and soft compliant foam. The surfaces should have sufficient roughness in order to transfer the motion to the skin without slippage, or minimizing such slippage. Additionally, the proper degree of surface roughness assures good lamellar action (transfer of lubricant from wet to dry portion of skin by interstitial spaces in the contacting surface). If the surface finish is too smooth the lubrication is wiped off and the contacting surface runs dry against skin and may cause unwanted abrasion of the skin. This surface roughness can be in the range of 5 to 20 micro-inches and preferably is 10 micro-inches.

Multiple contacting elements can be included, such that a set of skin contacting elements moving in one direction are interdigitated between a set of stationary skin contacting elements, or skin contacting elements moving in the opposing direction. FIG. 15 shows a device with a double pair of skin contacting elements, and is a derivative of the device with a single pair of skin contacting elements shown in FIG. 6. In the case shown in FIG. 15, each of two sets of skin contacting elements consists of three rows of bristle tufts. Each set of bristle tuft rows moves in relative opposition, surrounded by a fixed circuit row of fixed bristle tufts, which serve to minimize splashing and to control the contact of the moving bristle tips onto the skin. The bristle tufts are designed so that the interdigitated row movement results in sufficient force on the skin to maintain acroinfundibular openings. This action is similar to fingers of left and right hands interlocking while hand washing.

The model shown has three rows of bristles in each of the two interdigitated sets, but the number of bristle rows could vary from a single row to as many as practical for the desired surface area.

Additionally, the motion of the bristle tuft row(s) can be linear, arcuate or elliptical along the plane of the skin with the axis of rotation perpendicular to the skin.

The magnitude of reciprocal force applied to the skin is primarily determined by the stiffness of bristle tufts to lateral deformation, the length and width of the bristle rows, spacing between bristle rows, amplitude of interdigitated motion, and the pressure applied by the user.

The effects on the skin by the movement of the contacting elements can also be modified with the use of a skin lubricant. The lubricant can be water, soapy water, another skin cleaning agent, a lotion or gel. More lubrication results in more sliding action of the bristle tips across the skin, and less deforming action applied to the skin. The sliding action across the skin serves to remove skin surface debris. The debris includes sebum, triglycerides and fatty acids, desquamatized corneocytes and accumulated dirt and environmental materials.

Thus, the present invention provides either mechanical energy in a shear mode or tension/compression mode or a combination (elliptical) in order to loosen the adhesion between the sebaceous plug and the walls of the pore. Said motion can be produced by contact elements moving either reciprocally linearly, reciprocally arcuately or a combination thereof. The loosened sebaceous plug and any previously blocked lipids from the pores can then be readily removed by rinsing the cleansed area. Such an arrangement results in an effective treatment of early stage acne that prevents the development of more serious acne conditions. In addition, however, the arrangement can be used for effective cleansing of skin when acne is not present. The combination of gentleness and cleansing action produces a desirable, effective cleansing effect on the skin and a "sense" or feel by the user of clean, healthy skin.

Although the preferred embodiments of the invention has been disclosed for purposes of illustration, it should be understood that various substitutions and changes may be made in such embodiment, without departing from the spirit of the which is defined by the claims outlined below.

What is claimed is:

1. An apparatus for treatment of acne, comprising:
at least two contacting elements having end faces, all of the end faces being in substantially the same plane, wherein at least one contacting element is a moving contacting element, the end faces of the moving contacting element moving in a single plane;
a mounting assembly for holding the contacting elements substantially adjacent to each other; and
an assembly for positively moving said at least one moving contacting element bi-directionally about a neutral position relative to at least one adjacent contacting element, to produce alternating tension and compression of the skin, wherein when the apparatus is positioned so that the end faces of the contacting elements contact the skin, an action on the skin in the plane of a skin area to be treated for acne is produced to remove sebum plugs from skin pores, permitting ready removal thereof from the skin.

2. An apparatus of claim 1, wherein the frequency of movement of the moving contacting element is within a range of 20 Hz to 1 KHz.

3. An apparatus of claim 2, wherein the frequency is preferably within the range of 80-200 Hz.

4. An apparatus of claim 1, wherein the movement of the contacting element places the skin in alternating shear, which assists in loosening the sebaceous plugs from the skin pores in which they are located.

5. An apparatus of claim 4, wherein the movement of moving contact element is reciprocally arcuate in nature.

6. An apparatus of claim 1, wherein the contacting elements comprise, respectively, rows of bristle tufts.

7. An apparatus of claim 6, wherein the bristles have a diameter in the range of 2 to 5 mils and a length in the range of 0.250 to 0.600 inches, and wherein the bristle material has a flexural modulus in the range of 100 to 1000 kpsi.

8. An apparatus of claim 6 wherein the tufts have mechanical characteristics such that a displacement of 0.062 inches at the base of a tuft causes a force in the range of 0.3 grams to 1.4 grams, to be exerted on the skin at the end of said tuft.

9. An apparatus of claim 8 wherein the force is approximately 0.061 grams.

10. An apparatus of claim 6 wherein the peak amplitude of motion at the base of one bristle tuft with respect to that of an adjacent contacting element is in the range of 10%-125% of the center-to-center distance between adjacent contacting elements moving with respect to each other.

11. An apparatus of claim 10 wherein said peak amplitude of motion at the base of one bristle tuft with respect to that of an adjacent element is approximately 45%.

12. An apparatus of claim 6 wherein the rows of bristle tufts comprise a plurality of circular rows, alternating ones of which (a) move and (b) remain fixed in position.

13. An apparatus of claim 12 including a further row of fixed bristle tufts surrounding the plurality of circular rows.

14. An apparatus of claim 6 wherein the rows of bristle tufts comprise a plurality of circular rows, of which at least one circular row moves and at least one circular row is fixed in position.

15. An apparatus of claim 6 wherein the rows of bristle tufts comprise a plurality of circular rows, of which more than one circular row move and of which more than one circular row remain fixed in position.

16. An apparatus of claim 1, wherein the movement of the moving contacting element reciprocally places the skin in alternating tension and compression.

17. An apparatus of claim 1, wherein the motion of the moving contacting elements is controlled by a control means whereby the amplitude of motion of the moving contacting elements is substantially reduced when the contacting elements are not in contact with the skin and whereby the amplitude of motion of the moveable contacting elements is at the preferred magnitude when the contacting elements are applied to the skin with correct pressure for optimal operation and whereby the amplitude of motion of the moveable contacting elements is modified in a manner detectable by the user when the contacting elements are applied to the skin with greater than the correct pressure.

18. An apparatus of claim 1, including a fluid supplying structure positioned adjacent to the contacting elements and wherein said structure supplies a fluid which contacts the skin during operation.

19. An apparatus of claim 1, including a fluid-containing structure positioned adjacent the contacting elements and wherein said fluid-containing structure substantially prevents fluid from being expelled from the apparatus by movement of the contacting elements.

20. An apparatus of claim 19 wherein said fluid-containing structure consists of bristle tufts having a free end in approximately the same plane as that of the contacting elements.

21. An apparatus of claim 1, including a control assembly for controlling pressure applied to the skin so as to minimize the likelihood that excess skin pressure is exerted on the moving contacting elements.

22. An apparatus of claim 1, wherein said contacting elements are removable and replaceable.

23. An apparatus of claim 1, having a timing means, responsive to the device being turned on, for producing successive indications of intervals of elapsed time, wherein the intervals of elapsed time are related to desired times for treating portions of the face, wherein the successive indications of time are provided within a pre-established set period of time during which the apparatus is operating, and means for maintaining the status of the timing means for a selected period of time after the apparatus has been turned off during said pre-established period of time after the apparatus has been turned on.

24. An apparatus of claim 23 wherein the successive indications of time are provided within a pre-established set period of time during which the apparatus is operating.

25. An apparatus of claim 24 wherein the set period of time is approximately one minute and wherein the selected intervals of time are approximately 10 to 20 seconds.

26. An apparatus of claim 23 wherein the indications are a selected one of a) an audible signal and b) a detectable change in moving contacting element movement.

27. An apparatus of claim 23 wherein the indications comprise both an audible signal and a detectable change in moving contacting element movement.

28. An apparatus of claim 23 including means for changing the state of the timing means between enabled and disabled after the apparatus is turned on.

29. An apparatus of claim 28 wherein the changing means is responsive to an on/off switch being pressed on for a selected period of time.

30. An apparatus of claim 29 wherein a first audible signal indicates that the timing means has been enabled and a second audible signal different from the first audible signal indicates that the timing means has been disabled.

31. An apparatus for treatment of acne, comprising:
at least one moving contacting element having an end face for contacting the skin of a user; and an assembly for positively moving said contacting element bi-directionally about a neutral position to produce alternating tension and compression of the skin, such that when the apparatus is positioned so that the contacting element end face contacts the skin, an action on the skin in the plane of the skin area to be treated for acne is produced to remove sebum plugs from the skin pores, permitting ready removal thereof from the skin.

32. An apparatus of claim 31 wherein the frequency of movement of the contacting element is within a range of 80-200 Hz.

33. An apparatus of claim 31 wherein movement of the contacting element places the skin in alternating shear, which assists in loosening the sebaceous plugs from the skin pores in which they are located.

34. An apparatus of claim 31 wherein the contacting element has a peak-to-peak amplitude of within the range of 0.04 to 0.150 inches.

35. An apparatus of claim 31 wherein the contact element comprises a single row of bristle tufts.

36. An apparatus of claim 35 wherein the peak-to-peak amplitude of the motion of the bristle tufts is within the range of 0.020 to 0.160 inches.

37. An apparatus of claim 35 wherein the single row of bristle tufts is a circle.

38. An apparatus of claim 31 wherein the bristles have a diameter in the range of 2 to 5 mils, with a preferred diameter of 3 mils and a length in the range of 0.250 to 0.600 inches, with a preferred length of 0.430 inches, and wherein the bristle material has a flexural modulus in the range of 100 to 1000 kpsi, preferably 600 kpsi.

39. An apparatus of claim 31 wherein the movement of the contacting element reciprocally places the skin in alternating tension and compression.

40. An apparatus of claim 31 wherein the contact element comprises a plurality of rows of bristle tufts.

41. An apparatus of claim 40 wherein the plurality of rows of bristle tufts are circular.

42. An apparatus for treatment/cleansing of skin, comprising:
    at least two contacting elements having end faces, all of the end faces being in substantially the same plane, wherein at least one contacting element is a moving contacting element, the end faces of the moving contacting element moving in a single plane;
    a mounting assembly for holding the contacting elements substantially adjacent to each other; and
    an assembly for positively moving said at least one moving contacting element bi-directionally about a neutral position relative to at least one adjacent contacting element, to produce alternating tension and compression of the skin, wherein when the apparatus is positioned so that the end faces of the contacting elements contact the skin, an action on the skin in the plane of the skin area to be treated for acne produces a cleansing action on the skin, including removal of foreign material from skin pores.

43. An apparatus of claim 42 wherein the frequency of movement of the moving contacting element is within a range of 80-200 Hz.

44. An apparatus of claim 42 wherein relative movement of the contacting elements places the skin in alternating shear strain.

45. An apparatus of claim 42 wherein contacting elements comprise, respectively, rows of bristle tufts.

46. An apparatus of claim 42 wherein the movement of the moving contacting element reciprocally places the skin in alternating tension and compression.

47. An apparatus of claim 42 wherein the motion of the moving contacting elements is controlled by a control means whereby the amplitude of motion of the moving contacting elements is substantially reduced when the contacting elements are not in contact with the skin and whereby the amplitude of motion of the moveable contacting elements is at the preferred magnitude when the contacting elements are applied to the skin with correct pressure for optimal operation and whereby the amplitude of motion of the moveable contacting elements is modified in a manner detectable by the user when the contacting element are applied to the skin with greater than the correct pressure.

48. An apparatus of claim 42 including a fluid supplying structure positioned adjacent to the contacting elements and wherein said structure supplies a fluid which contacts the skin during operation.

49. An apparatus of claim 42 wherein said contacting elements are removable and replaceable.

50. An apparatus of claim 42 having a timing means, responsive to the device being turned on, for producing successive indications of intervals of elapsed time, wherein the intervals of elapsed time are related to desired times for treating portions of the face, wherein the successive indications of time are provided within a pre-established set period of time during which the apparatus is operating; and means for maintaining the status of the timing means for a selected period of time after the apparatus has been turned off during said pre-established period of time after the apparatus has been turned on.

51. An apparatus of claim 42 wherein the rows of bristle tufts comprise a plurality of circular rows, which at least one circular row moves and at least one circular row is fixed in position.

52. An apparatus of claim 42 wherein the rows of bristle tufts comprise a plurality of circular rows, of which more than one circular row move and of which more than one circular row remain fixed in position.

* * * * *

(12) EX PARTE REEXAMINATION CERTIFICATE (8557th)
United States Patent
Pilcher et al.

(10) Number: US 7,320,691 C1
(45) Certificate Issued: Sep. 20, 2011

(54) APPARATUS AND METHOD FOR ACOUSTIC/MECHANICAL TREATMENT OF EARLY STAGE ACNE

(75) Inventors: Kenneth A. Pilcher, Seattle, WA (US); David Giuliani, Mercer Island, WA (US); Stephen M. Meginniss, Seattle, WA (US)

(73) Assignee: Pacific Bioscience Laboratories, Seattle, WA (US)

Reexamination Request:
No. 90/009,797, Aug. 4, 2010
No. 90/011,343, Nov. 19, 2010

Reexamination Certificate for:
Patent No.: 7,320,691
Issued: Jan. 22, 2008
Appl. No.: 10/345,909
Filed: Jan. 15, 2003

(51) Int. Cl.
*A61B 17/50* (2006.01)

(52) U.S. Cl. .......... 606/131; 604/289; 604/313
(58) Field of Classification Search ............ None
See application file for complete search history.

(56) References Cited

U.S. PATENT DOCUMENTS

| | | | |
|---|---|---|---|
| 3,968,789 | A | 7/1976 | Simoncini |
| 4,027,348 | A | 6/1977 | Flowers et al. |
| 4,378,804 | A | 4/1983 | Cortese, Jr. |
| 4,738,001 | A | 4/1988 | Shipp |
| 5,189,751 | A | 3/1993 | Giuliani et al. |
| 5,309,590 | A | 5/1994 | Giuliani et al. |
| 5,416,942 | A | 5/1995 | Baldacci et al. |
| 5,544,382 | A | 8/1996 | Giuliani et al. |
| 5,647,841 | A | 7/1997 | Groenewold |
| 5,815,872 | A | 10/1998 | Meginniss, III et al. |
| 5,994,855 | A | 11/1999 | Lundell et al. |
| 6,170,108 | B1 | 1/2001 | Knight |

*Primary Examiner* — Beverly M. Flanagan

(57) ABSTRACT

The apparatus includes at least two skin-contacting elements, the elements having narrow end faces and a mounting assembly for holding the elements closely adjacent to each other. A driving assembly reciprocally moves one element relative to the adjacent element(s) at a frequency that produces an action on the pores of the skin to loosen sebaceous plugs present in the pores, by permitting their ready removal from the skin.

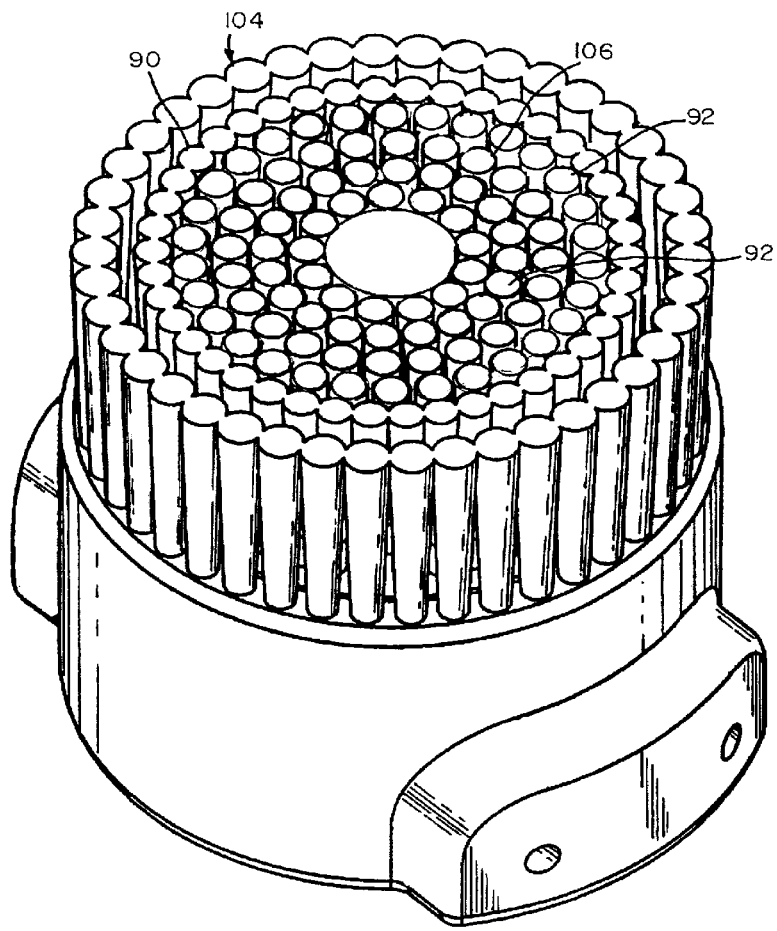

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-52 is confirmed.

New claims 53-64 are added and determined to be patentable.

53. *An apparratus for treatment of acne, comprising:*
   *at least one moving contacting element having an end face for contacting the skin of a user, wherein the at least one moving contacting element comprises one or more circular rows of bristle tufts; and*
   *an assembly for positively moving said at least one moving contacting element bi-directionally about a neutral position in a reciprocally arcuate manner to produce alternating tension and compression of the skin such that when the apparatus is positioned so that the end face contacts the skin, an action on the skin in the plane of the skin area to be treated for acne is produced to remove sebum plugs from the skin pores, permitting ready removal thereof from the skin, wherein a frequency of movement of the at least one moving contacting element is within a range of 20 Hz to 1 kHz.*

54. *The apparatus of claim 53, wherein the frequency of movement is within a range of 80-200 Hz.*

55. *The apparatus of claim 53, wherein one or more bristles of the one or more circular rows of bristle tufts has a diameter in the range of 2-5 mils and a length in the range 0.250-0.600 inches, and wherein a material out of which the one or more bristles is made has a flexural modulus in the range of 100-1000 kpsi.*

56. *The apparatus of claim 53, wherein the at least one moving contacting element has a peak-to-peak amplitude within a range of 0.04-0.150 inches.*

57. *The apparatus of claim 53, wherein the frequency of movement is within a range of 80-200 Hz, wherein one or more bristles of the one or more circular rows of bristle tufts has a diameter in the range of 2-5 mils and a length in the range of 0.250-0.600 inches, wherein a material out of which the one or more bristles is made has a flexural modulus in the range of 100-1000 kpsi and wherein the at least one contacting element has a peak-peak amplitude of 0.04-0.150 inches.*

58. *The apparatus of claim 53, wherein one or more tufts of the one or more circular rows of bristle tufts has mechanical characteristics such that a displacement of 0.062 inches at the base of the tuft causes a force in the range of 0.3 grams to 1.4 grams to be exerted on the skin at the end of said tuft.*

59. *An apparatus for treatment/cleansing of skin, comprising:*
   *at least two contacting elements having end faces, all of the end faces being in substantially the same plane, wherein at least one contacting element is a moving contacting element, the end faces of the moving contacting element moving in a single plane, wherein said at least one contacting element comprises one or more circular rows of bristle tufts;*
   *a mounting assembly for holding the contacting elements substantially adjacent to each other; and*
   *an assembly for positively moving said at least one moving contacting element bi-directionally about a neutral position relative to at least one adjacent contacting element, to produce alternating tension and compression of the skin, wherein when the apparatus is positioned so that the end faces of the contacting elements contact the skin, an action on the skin in the plane of the skin area to be treated for acne produces a cleansing action on the skin, including removal of foreign material from skin pores, wherein a frequency of movement of said at least one contacting element is within a range of 20 Hz to 1 kHz.*

60. *The apparatus of claim 59, wherein the frequency of movement is within a range of 80-200 Hz.*

61. *The apparatus of claim 59, wherein one or more bristles of the one or more circular rows of bristle tufts has a diameter in the range of 2 to 5 mils and a length in the range of 0.250 to 0.600 inches and wherein a material out of which the bristle is made has a flexural modulus in the range of 100 to 1000 kpsi.*

62. *The apparatus of claim 59, wherein the at least one moving contacting element has a peak-to-peak amplitude within a range of 0.04 to 0.0150 inches.*

63. *The apparatus of claim 59, wherein the frequency of movement is within a range of 80-200 Hz, wherein one or more bristles of the one or more circular rows of bristle tufts has a diameter in the range of 2 to 5 mils and a length in the range of 0.250 to 0.600 inches, and wherein a material out of which the one or more bristles is made has a flexural modulus in the range of 100 to 1000 kpsi and wherein the at least one moving contacting element has a peak-to-peak amplitude within a range of 0.04-0.0150 inches.*

64. *The apparatus of claim 59, wherein one or more tufts of the one or more circular rows of bristle tufts has mechanical characteristics such that a displacement of 0.062 inches at the base of the one or more tufts causes a force in the range of 0.3 grams to 1.4 grams to be exerted on the skin of the under said tuft.*

\* \* \* \* \*